(12) United States Patent
Weibel et al.

(10) Patent No.: US 11,185,629 B2
(45) Date of Patent: Nov. 30, 2021

(54) DOSING APPARATUS AND INJECTION DEVICE

(71) Applicant: SHL Medical AG, Zug (CH)

(72) Inventors: Ludwig Daniel Weibel, Waldstatt (CH); Samuel Wyler, Abtwil (CH); Christoph Egloff, Löhningen (CH)

(73) Assignee: SHL MEDICAL AG, Zug (CH)

( * ) Notice: Subject to any disclaimer, the term of this patent is extended or adjusted under 35 U.S.C. 154(b) by 125 days.

(21) Appl. No.: 16/305,210

(22) PCT Filed: Jun. 7, 2017

(86) PCT No.: PCT/EP2017/063750
§ 371 (c)(1),
(2) Date: Nov. 28, 2018

(87) PCT Pub. No.: WO2017/211851
PCT Pub. Date: Dec. 14, 2017

(65) Prior Publication Data
US 2019/0201617 A1    Jul. 4, 2019

(30) Foreign Application Priority Data

Jun. 8, 2016 (EP) ..................................... 16173561

(51) Int. Cl.
*A61M 5/158* (2006.01)
*A61M 5/142* (2006.01)
(Continued)

(52) U.S. Cl.
CPC ................ *A61M 5/158* (2013.01); *A61J 1/20* (2013.01); *A61M 5/1422* (2013.01);
(Continued)

(58) Field of Classification Search
CPC ................ A61M 5/158; A61M 5/1422; A61M 5/14244; A61M 5/14248; A61M 5/16809;
(Continued)

(56) References Cited

U.S. PATENT DOCUMENTS 1,689,419 A * 10/1928 Bronander .............. F04B 7/045
                                                  417/488
3,451,393 A    6/1969 Sarnoff
(Continued)

FOREIGN PATENT DOCUMENTS

AU    2010207762 A1    9/2010
CH       700473 A1    8/2010
(Continued)

OTHER PUBLICATIONS

European Search Report Corresponding to 16173561.8 dated Jan. 2, 2017.
(Continued)

*Primary Examiner* — Tiffany Legette
*Assistant Examiner* — Antarius S Daniel
(74) *Attorney, Agent, or Firm* — McDonnell Boehnen Hulbert & Berghoff LLP

(57) ABSTRACT

An injection device for subcutaneous delivery of fluid which comprises a puncture cannula and an indwelling cannula. In a starting position, a distal end region of the puncture cannula runs coaxially inside the indwelling cannula. The device comprises displaceably mounted first and second runners. The first runner is connected to the puncture cannula and the second runner to the indwelling cannula. A control element is movable over a predefined control area. The control element is configured such that, in a first part of the control area, the control element effects an equidirectional displacement of the first and the second runners, and hence fitting of the indwelling cannula and, in a second part (Continued)

Figure 1:
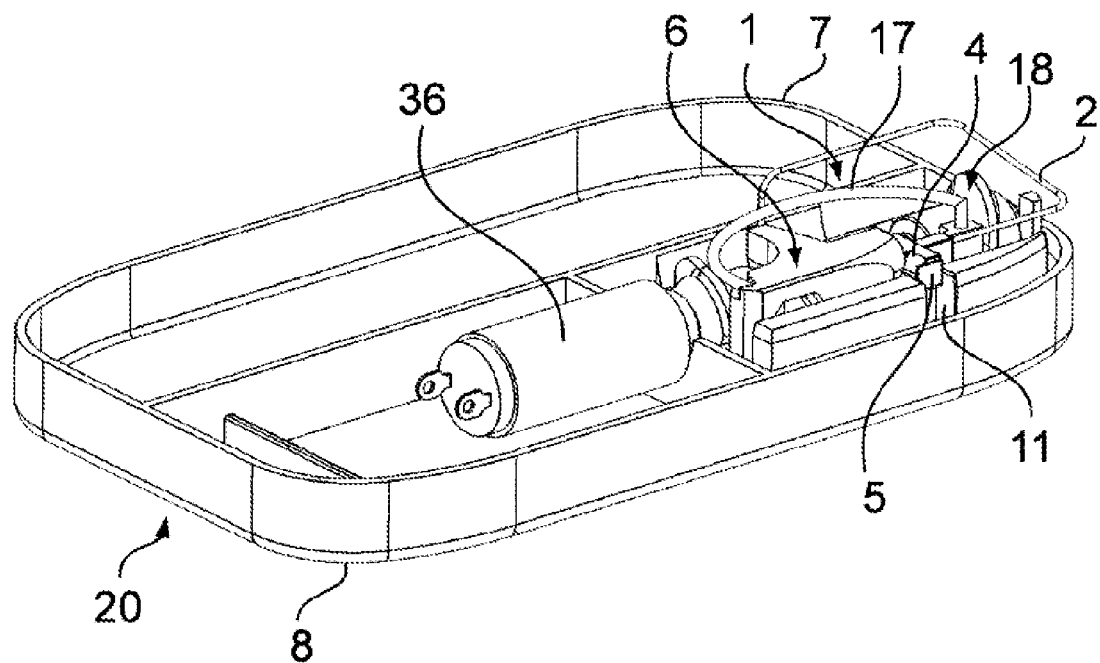

of the control area, effects blocking of the second runner, and hence holding of the indwelling cannula in a dwell position, and return of the first runner and withdrawal of the puncture cannula into an end position.

13 Claims, 14 Drawing Sheets

(51) Int. Cl.
*A61M 5/168* (2006.01)
*A61J 1/20* (2006.01)
*A61M 25/06* (2006.01)

(52) U.S. Cl.
CPC .... *A61M 5/14244* (2013.01); *A61M 5/14248* (2013.01); *A61M 5/16809* (2013.01); *A61M 25/0606* (2013.01); *A61M 2005/14252* (2013.01); *A61M 2005/1585* (2013.01)

(58) Field of Classification Search
CPC ............ A61M 5/14216; A61M 5/1407; A61M 2005/1581; A61M 2005/1585; A61M 2005/14252; A61M 25/0606; A61M 2005/14533; A61M 2005/14256; A61M 5/145; A61M 5/1452; A61J 1/20; F04B 19/20; F04B 19/22; F04B 1/0426; F04B 1/0417; F04B 1/0413
See application file for complete search history.

(56) References Cited

U.S. PATENT DOCUMENTS

| | | | |
|---|---|---|---|
| 5,267,963 A | 12/1993 | Bachynsky | |
| 5,876,380 A | 3/1999 | Manganini et al. | |
| 5,931,814 A | 8/1999 | Alex et al. | |
| 6,277,091 B1 | 8/2001 | Genet | |
| 6,659,978 B1 | 12/2003 | Kasuga et al. | |
| 6,679,248 B2 | 1/2004 | Stadelhofer | |
| 6,902,543 B1 | 6/2005 | Cherif-Cheikh et al. | |
| 7,470,253 B2 | 12/2008 | Kriesel et al. | |
| 7,837,653 B2 | 11/2010 | Kriesel et al. | |
| 8,547,239 B2 | 10/2013 | Peatfield et al. | |
| 8,702,405 B2 * | 4/2014 | Verrilli | F04B 3/00 417/461 |
| 9,173,993 B2 | 11/2015 | Yodfat et al. | |
| 9,566,384 B2 | 2/2017 | Gyrn et al. | |
| 2001/0025168 A1 | 9/2001 | Gross et al. | |
| 2003/0135159 A1 | 7/2003 | Daily et al. | |
| 2004/0010207 A1 | 1/2004 | Flaherty et al. | |
| 2004/0049129 A1 | 3/2004 | Qi | |
| 2007/0060875 A1 | 3/2007 | Bassarab et al. | |
| 2007/0060876 A1 | 3/2007 | Bassarab et al. | |
| 2007/0060877 A1 | 3/2007 | Bassarab et al. | |
| 2007/0129673 A1 | 6/2007 | Bassarab et al. | |
| 2008/0215006 A1 | 9/2008 | Thorkild | |
| 2008/0228144 A1 | 9/2008 | Liniger et al. | |
| 2009/0043278 A1 | 2/2009 | Tanaka et al. | |
| 2009/0093792 A1 | 4/2009 | Gross et al. | |
| 2009/0105646 A1 | 4/2009 | Hendrixson et al. | |
| 2009/0131864 A1 | 5/2009 | Pickhard | |
| 2009/0204077 A1 | 8/2009 | Hasted et al. | |
| 2009/0292245 A1 | 11/2009 | Basso et al. | |
| 2010/0087799 A1 | 4/2010 | Galbraith et al. | |
| 2010/0130931 A1 | 5/2010 | Yodfat et al. | |
| 2010/0130932 A1 * | 5/2010 | Yodfat | F04B 43/1269 604/151 |
| 2010/0262074 A1 | 10/2010 | Seiferlein et al. | |
| 2010/0274186 A1 | 10/2010 | Seiferlein et al. | |
| 2011/0021990 A1 * | 1/2011 | Navarro | A61M 5/14216 604/151 |
| 2011/0034883 A1 | 2/2011 | Gyrn et al. | |
| 2011/0036844 A1 | 2/2011 | Gyrn et al. | |
| 2011/0040263 A1 * | 2/2011 | Hordum | A61M 5/14248 604/272 |
| 2011/0046456 A1 | 2/2011 | Hordum et al. | |
| 2011/0060274 A1 | 3/2011 | Kuhn | |
| 2011/0073620 A1 | 3/2011 | Verrilli | |
| 2011/0077588 A1 | 3/2011 | Hirschel et al. | |
| 2011/0098652 A1 | 4/2011 | Hasted et al. | |
| 2011/0130723 A1 | 6/2011 | Hirschel et al. | |
| 2011/0301534 A1 | 12/2011 | Renz et al. | |
| 2013/0338592 A1 | 12/2013 | Calasso | |
| 2014/0058360 A1 | 2/2014 | Schoonmaker et al. | |
| 2014/0114240 A1 | 4/2014 | Joedicke et al. | |
| 2014/0158700 A1 | 6/2014 | Glocker et al. | |
| 2014/0316378 A1 | 10/2014 | Magnenat et al. | |
| 2014/0332559 A1 | 11/2014 | Ritzenhoff et al. | |
| 2014/0334252 A1 | 11/2014 | Harand et al. | |
| 2015/0196719 A1 * | 7/2015 | Uchiyama | A61M 5/3287 604/156 |
| 2015/0209518 A1 | 7/2015 | Moser et al. | |
| 2016/0121043 A1 | 5/2016 | Weibel | |
| 2016/0213851 A1 | 7/2016 | Weibel et al. | |
| 2017/0246386 A1 | 8/2017 | Gyrn et al. | |

FOREIGN PATENT DOCUMENTS

| | | |
|---|---|---|
| CN | 101 687 075 A | 3/2010 |
| CN | 101939033 A | 1/2011 |
| CN | 103328022 A | 9/2013 |
| CN | 104619365 A | 5/2015 |
| CN | 104797279 A | 7/2015 |
| EP | 2 259 816 B1 | 10/2015 |
| FR | 2799643 | 1/2000 |
| TW | 201603850 A | 2/2016 |
| WO | 8606967 A1 | 12/1986 |
| WO | 9523576 A1 | 9/1995 |
| WO | 9915215 A1 | 4/1999 |
| WO | 0126718 A1 | 4/2001 |
| WO | 0172354 A2 | 10/2001 |
| WO | 0202165 A2 | 1/2002 |
| WO | 0224259 A2 | 3/2002 |
| WO | 0240083 A2 | 5/2002 |
| WO | 03090509 A2 | 11/2003 |
| WO | 2004058327 A2 | 7/2004 |
| WO | 2004089448 A1 | 10/2004 |
| WO | 2006031500 A2 | 3/2006 |
| WO | 2006045132 A2 | 5/2006 |
| WO | 2006057636 A1 | 6/2006 |
| WO | 2007020237 A1 | 2/2007 |
| WO | 2007020238 A2 | 2/2007 |
| WO | 2007020239 A1 | 2/2007 |
| WO | 2007020240 A1 | 2/2007 |
| WO | 2008040478 A1 | 4/2008 |
| WO | 2008063439 A2 | 5/2008 |
| WO | 2008107378 A1 | 9/2008 |
| WO | 2008122360 A2 | 10/2008 |
| WO | 2008/139458 A2 | 11/2008 |
| WO | 2008150715 A1 | 12/2008 |
| WO | 2008151736 A1 | 12/2008 |
| WO | 2008151737 A1 | 12/2008 |
| WO | 2009039013 A1 | 3/2009 |
| WO | 2009077091 A1 | 6/2009 |
| WO | 2009088608 A2 | 7/2009 |
| WO | 2009/098306 A1 | 8/2009 |
| WO | 2009/103759 A1 | 8/2009 |
| WO | 2009098291 A1 | 8/2009 |
| WO | 2009100549 A1 | 8/2009 |
| WO | 2009100550 A1 | 8/2009 |
| WO | 2009101130 A1 | 8/2009 |
| WO | 2009101145 A1 | 8/2009 |
| WO | 2009103759 A1 | 8/2009 |
| WO | 2009106517 A1 | 9/2009 |
| WO | 2009158659 A2 | 12/2009 |
| WO | 2010022069 A2 | 2/2010 |
| WO | 2010077278 A1 | 7/2010 |
| WO | 2010085904 A1 | 8/2010 |
| WO | 2011004333 A1 | 1/2011 |
| WO | 2011056375 A2 | 5/2011 |
| WO | 2011075105 A1 | 6/2011 |
| WO | 2011101351 A1 | 8/2011 |

(56) References Cited

FOREIGN PATENT DOCUMENTS

| | | |
|---|---|---|
| WO | 2012068321 A1 | 5/2012 |
| WO | 2012072533 A1 | 6/2012 |
| WO | 2012072541 A1 | 6/2012 |
| WO | 2012072554 A1 | 6/2012 |
| WO | 2012072556 A1 | 6/2012 |
| WO | 2012072559 A1 | 6/2012 |
| WO | 2012/103428 A2 | 8/2012 |
| WO | 2012103316 A1 | 8/2012 |
| WO | 2012110474 A1 | 8/2012 |
| WO | 2012116948 A1 | 9/2012 |
| WO | 2012126636 A1 | 9/2012 |
| WO | 2012135537 A2 | 10/2012 |
| WO | 2012146674 A1 | 11/2012 |
| WO | 2012152668 A1 | 11/2012 |
| WO | 2012152694 A1 | 11/2012 |
| WO | 2012152703 A1 | 11/2012 |
| WO | 2012152704 A1 | 11/2012 |
| WO | 2012160156 A2 | 11/2012 |
| WO | 2012160167 A1 | 11/2012 |
| WO | 2013019850 A2 | 2/2013 |
| WO | 2013033227 A2 | 3/2013 |
| WO | 2013092934 A1 | 6/2013 |
| WO | 2013167494 A1 | 11/2013 |
| WO | 2014005953 A1 | 1/2014 |
| WO | 2014/090745 A1 | 6/2014 |
| WO | 2014179774 A1 | 11/2014 |
| WO | 2014/191038 A2 | 12/2014 |
| WO | 2014204457 A1 | 12/2014 |
| WO | 2014204894 A2 | 12/2014 |
| WO | 2015018787 A1 | 2/2015 |
| WO | 2015022295 A2 | 2/2015 |
| WO | 2015032745 A1 | 3/2015 |
| WO | 2015074641 A1 | 5/2015 |
| WO | 2015118358 A1 | 8/2015 |
| WO | 2015/164645 A1 | 10/2015 |
| WO | 2015164645 A1 | 10/2015 |
| WO | 2015164650 A1 | 10/2015 |
| WO | 2016034683 A1 | 3/2016 |
| WO | 2016055445 A1 | 4/2016 |
| WO | 2016067179 A1 | 5/2016 |
| WO | 2016071483 A1 | 5/2016 |
| WO | 2016154413 A1 | 9/2016 |
| WO | 2016172182 A1 | 10/2016 |
| WO | 2017080814 A1 | 5/2017 |
| WO | 2017129191 A1 | 8/2017 |
| WO | 2017160625 A1 | 9/2017 |
| WO | 2017160626 A1 | 9/2017 |
| WO | 2017214392 A1 | 12/2017 |
| WO | 2017214405 A1 | 12/2017 |
| WO | 2017214415 A1 | 12/2017 |
| WO | 2017214424 A2 | 12/2017 |
| WO | 2018002314 A1 | 1/2018 |
| WO | 2018018166 A1 | 2/2018 |
| WO | 2018024625 A1 | 2/2018 |
| WO | 2018029238 A1 | 2/2018 |
| WO | 2018096149 A1 | 5/2018 |

OTHER PUBLICATIONS

International Search Report Corresponding to PCT/EP2017/063750 dated Feb. 16, 2018.
Written Opinion Corresponding to PCT/EP2017/063750 dated Feb. 16, 2018.
Chinese Office Action for CN Application No. 201780035535.4, dated Dec. 1, 2020.

* cited by examiner

DOSING APPARATUS AND INJECTION DEVICE

The present invention relates to a dosing apparatus, its use for the, in particular subcutaneous, delivery of a fluid, and to an injection device for the subcutaneous delivery of a fluid, according to the preambles of the independent claims. Independently thereof, the present invention also relates respectively to a dosing apparatus of this type and to an injection device of this type, which, alternatively or additionally to the subcutaneous delivery, is respectively suitable for the intradermal, intramuscular or intraperitoneal delivery of a fluid, as well as to the use thereof. In the administration of liquid formulations of pharmaceutical agents, it is in most cases necessary to deliver well defined volumes. Often drugs must here be injected into the body of a patient. For the parenteral injection, hypodermic syringes, drug pens or drug pumps are employed. In particular in the case of preparations which have to be administered over a lengthy period and/or according to a precisely specified schedule, syringes and pens are increasingly being replaced by drug pumps. Thus, patients suffering from diabetes, for instance, often administer an insulin dose to themselves several times a day under strongly varying conditions. In just such an application, the use of a drug pump represents a significant simplification for the patient, since the handling of such a pump means a markedly lesser restriction than that of a syringe or a pen.

Depending on the design, drug pumps are suitable for being attached over lengthy period to the body of a patient and for administrating a preparation continuously and/or according to an individually specified schedule. Drug pumps of this type typically comprise a container for the liquid formulation, and a conveying device, which conveys the drug to a port of the device or to an injection system. Such an injection system can be suitable for fitting an indwelling cannula, which remains in the body of the patient throughout the administration period.

Thus, WO 2014/191038 A1 shows a dosing apparatus for the subcutaneous delivery of a fluid. Said apparatus comprises an injection device having a flexible indwelling cannula, wherein a puncture cannula runs coaxially inside the indwelling cannula in order to support the latter in the course of the fitting. After the fitting process, the puncture cannula is withdrawn from the indwelling cannula in order to make the delivery less disagreeable for the patient. Besides the injection device, said apparatus further comprises a collapsible container having an interior for receiving the fluid. The container is connected via a closure piece to a conveying device, which is configured as a valveless positive displacement piston pump. The dosing apparatus enables a fully automatic subcutaneous delivery of a fluid to a patient.

However, the apparatus, in terms of its mechanics, is of comparatively complex design. Thus, the conveying device and the injection device form two completely independent units. These are respectively composed of a large number of individual parts, which makes manufacture more cost-intensive and is detrimental to reliability in application.

WO 2009/098306 A1 relates to an injection device in which the fitting of an indwelling cannula is obtained with the aid of a puncture cannula via a slotted guide. Although the movements of the indwelling cannula and of the puncture cannula are mechanically coupled in a constructively simple and reliable manner via the slotted guide, the described device is still comparatively awkward to use. On the one hand, the actual injection device, after the fitting of the indwelling cannula, must be removed from a base plate attached to the skin of a patient. On the other hand, a fluidic connection must be created between the indwelling cannula and the fluid source. An automatic usage of the device is hence not possible. In design terms too, said device has some drawbacks. Thus, special latching means for the indwelling cannula are necessary on the base plate. Furthermore, the injection device has a comparatively large construction height.

The object of the present invention is therefore to overcome the drawbacks in the prior art.

In particular, it is an object of the present invention to provide a widely applicable and constructively simple dosing apparatus for the, in particular subcutaneous, delivery of a fluid, and an injection device for the subcutaneous delivery of a fluid. These should be able to be manufactured in a simple and hence cost-effective manner in terms of their mechanics. Furthermore, they should be user-friendly in respect of their application, enable automatic use and have high reliability.

Where necessary, the present invention should also, alternatively or additionally to the subcutaneous delivery, be suitable for the intradermal, intramuscular or intraperitoneal delivery of a fluid.

These objects are achieved by a dosing apparatus and an injection device which exhibit the features in the independent claims.

An injection device for the subcutaneous delivery of a fluid comprises a puncture cannula and an indwelling cannula. In a starting position, a distal end region of the puncture cannula runs coaxially inside the indwelling cannula. The device comprises a first and a second displaceably mounted runner. The first runner is connected to the puncture cannula and the second runner to the indwelling cannula. The injection device further comprises a control element, which is movable over a predefined control area and which, for the displacement of the first runner and of the second runner, can be brought into operative connection with these. The control element is configured such that, in a first part of the control area, it effects an equidirectional, in particular simultaneous, displacement of the two runners, and hence a fitting of the indwelling cannula. Furthermore, the control element is configured such that, in a second part of the control area, it effects a blocking of the second runner, and hence a holding of the indwelling cannula in a dwell position, as well as a backshift of the first runner, and hence a withdrawal of the puncture cannula from the distal end region of the indwelling cannula into an end position.

Independently thereof, the present invention also relates to an injection device of the type which, alternatively or additionally to the subcutaneous delivery, is suitable for the intradermal, intramuscular or intraperitoneal delivery of a fluid, and its use.

By virtue of this mechanical design of the injection device, a puncture-cannula-assisted fitting of the indwelling cannula, followed by a withdrawal of the puncture cannula, can be reliably effected. The mechanism makes do with a small number of individual parts, whereby it can be manufactured in a cost-effective manner and is reliable in its application.

The runners can be mounted displaceably via a guide device, preferably via a common guide device, in particular via a linear guide. The use of a common guide device enables the number of individual parts of the injection device to be further reduced. In particular, a linear guide enables a simplification of the mechanism.

Thus, the runners can be mounted displaceably via a common linear guide and the linear guide can be oriented in a fitting direction parallel to the distal end regions of the puncture cannula and of the indwelling cannula. Hence the linear guide prescribes not only the direction of displacement of the first and of the second runner, but also the fitting direction of the injection device. This can hence be defined in advance and adapted to the respective application of the device. Thus, it is possible, for instance, to design the injection device such that the indwelling cannula is fitted substantially perpendicularly under the skin of the patient.

The control element can be mounted movably, in particular displaceably, in a direction in particular substantially perpendicular to that of the linear guide. This enables an optimal force transmission from the control element to the first and the second runner in both directions.

The control element can be configured as a displaceable cam carrier. A cam carrier has the advantage that, with this, almost any movement which is representable via a constantly differentiable function can be specified. The control element can be configured as a pair of congruent, displaceable cam carriers, which pair acts on both sides on the runners. This enables the force to be transmitted in a particularly effective manner from the control element to the runners. Since the force transmission is realized on both sides, it is possible to prevent a torque from being at the same time transmitted to the runners. A tilting of these same in a guide device can thereby be avoided.

The control element can comprise a first and a second portion. The first portion can effect an equidirectional, in particular simultaneous, displacement of the two runners, and hence a fitting of the indwelling cannula. The second portion can effect a blocking of the second runner, and hence a holding of the indwelling cannula in a dwell position, as well as a retreat of the first runner, and hence a withdrawal of the puncture cannula from the distal end region of the indwelling cannula into an end position. In particular different sides of the second portion can here act on the first and on the second runner. Through the division of the control element into two portions, this can be designed particularly simply in terms of its geometry. The movement of the first runner and of the second runner can be specified by cam surfaces on the control element.

The control element can be pretensioned via a spring element, in particular via a helical spring. This enables an autonomous displacement of the control element to be effected in a constructively simple manner without a further, separate drive being necessary for this purpose.

However, the control element can also be movable via a helical gear, in particular via a worm gear. As a result, the control element can be easily moved by a rotary drive with the necessary gear reduction.

However, the control element can also be movable via a barrel cam and/or holdable against a spring preload. In contrast to a helical gear, a barrel cam enables the implementation of more complex motional sequences of the control element. Thus, it is conceivable, for instance, that the barrel cam must first rotate through a predefined angle until the control element is released and is movable by the spring preload. In much the same way as with the control element itself, with a barrel cam all movements which are describable by a constantly differentiable function are in principle realizable. Thus, it is conceivable, for instance, that the control element, driven by the barrel cam, moves in different parts of the control area in different directions or at different speed.

The second runner can be designed as a holding plate. A holding plate has the advantage that it is more easily producible in comparison to an injection molded part. Given the same wall thickness, moreover, it has a greater mechanical load bearing capacity. It can therefore be designed comparatively flat, whereby the total construction height of the injection device can be reduced. Moreover, the holding plate, if so desired, can display a certain resilience.

A transition from the puncture cannula to the indwelling cannula can be sealed with a sealing element. In the dwell position the sealing element can be squeezed, in particular by a wall portion of a dosing apparatus and the second runner. A particularly fluidtight transition from the puncture cannula to the indwelling cannula can hence be obtained. Obviously, this design of the injection device can also be realized independently of other features of the device.

The indwelling cannula can have a flange or a flange-like region having increased wall thickness. In the dwell position, the flange, or the flange-like region, can be squeezed, in particular by a wall portion of a dosing apparatus and the second runner. As a result, a holding of the indwelling cannula can be obtained. This can be in particular of importance when the dosing apparatus is removed from the skin of a patient and the indwelling cannula, inter alia, is withdrawn from his or her skin. An unintended sticking of the indwelling cannula can thereby namely be avoided.

The puncture cannula can be configured as a hollow needle. This design enables the puncture cannula to simultaneously perform a conducting function and a penetration function. The puncture cannula can here be formed in one continuous piece, in particular from steel. Accordingly, sealing problems between different line portions can be avoided. The proximal end region of the puncture cannula can be arranged rigidly in fixed location. As a result, a fluidtight connection, for instance to a conveying device, can be easily ensured. In particular, the distal end region of the puncture cannula can in the end position remain in the proximal end region of the indwelling cannula. This enables a transfer of fluid from the puncture cannula to the indwelling cannula in a constructively simple manner. In particular, in the end position, by the puncture cannula and the indwelling cannula, a fluid path for the, in particular subcutaneous, intradermal, intramuscular or intraperitoneal delivery of a fluid can be formed.

The blocking of the second runner, and hence the holding of the indwelling cannula in the dwell position, can be realized merely by action of the control element on the second runner, in particular by exertion of a compressive force. Hence a further design simplification of the injection device is obtained. The use of additional means for holding the indwelling cannula, for instance of latching elements, is no longer necessary.

Through the movement of the control element over the control area, a lever element can additionally be movable, in particular by an additional cam surface of the control element, from a first position into at least a second position, and hence, in particular, rotatable around a rotational axis. As a result, further functions can be controlled by the control element. For instance, it is conceivable that, after the fitting of the indwelling cannula, a valve device or conveying device is activated, whereby a liquid to be delivered can be conducted to the injection device. This increases the reliability of a device of this type and makes this less prone to incorrect manipulations by a user.

A further aspect of the present invention relates to a dosing apparatus for the, in particular subcutaneous, delivery of a fluid. Said dosing apparatus can comprise a conveying device for conveying the fluid out of the interior of a container. The fluid is here conveyable by means of the conveying device from the container to a delivery opening. The dosing apparatus can comprise a housing having an external contact surface, via which the apparatus is attachable, in particular, to the body of a patient. The dosing apparatus is hence suitable for the delivery of a fluid according to a predefined schedule and/or over a lengthy period, in particular in the case of a mobile patient.

Independently thereof, the present invention also relates to a dosing apparatus of this type, which, alternatively or additionally to the subcutaneous delivery, is suitable for the intradermal, intramuscular or intraperitoneal delivery of a fluid, and its use.

A dosing apparatus of this type can comprise an injection device as described above. Thus, the puncture cannula and the indwelling cannula can be arranged, in a starting position, substantially within the housing and, for the fitting of the indwelling cannula, can be extensible from the housing through a fitting opening on the contact surface. In particular in the case of a dosing apparatus attached to the body of a patient, the fitting of the indwelling cannula can hence be realized fully automatically. This facilitates the handling of the apparatus by a patient.

If the runners of the injection device are mounted displaceably via a guide device, preferably via a common guide device, in particular via a linear guide, the guide device can be an integral component part of the housing. The dosing apparatus can thereby be produced more simply.

The conveying device can be designed as a positive displacement pump, preferably as a valveless piston pump, preferredly as a valveless double piston pump. Specifically the use of a piston pump is in this context advantageous, since with such a pump higher pressures can be obtained than with, for instance, a peristaltic pump. By virtue of a valveless design, a contamination of the conveyed fluid is more easily able to be prevented. A double-piston pump is particularly well suited for the valveless design. Furthermore, this pump type affords great versatility in terms of the feasible applications. In addition, specifically in pharmaceutical formulations which are based on a biopolymer as the active agent], shearing forces generated by the conveying device cause a decomposition of the active agent. This adverse effect can be very largely avoided through the use of said pumps.

Thus, the conveying device can comprise a cylinder, having at least one intake opening and at least one outlet opening on a cylinder inner wall, and a first and a second piston. The first piston and the second piston can be mounted displaceably within the cylinder in the longitudinal direction. The first piston and the second piston can here delimit between their end faces, jointly with a portion of the cylinder inner wall, a variable fluid volume. In particular parallelly alongside the cylinder can be arranged a barrel cam having a first and a second cam structure. The first cam structure can be in operative connection with the first piston, and the second cam structure with the second piston. Upon a rotation of the barrel cam, the first cam structure can prescribe the stroke movement of the first piston, and the second cam structure the stroke movement of the second piston. The use of a double-piston pump enables a particularly simple and effective control of the two pistons. In particular when the barrel cam is arranged parallelly alongside the cylinder of the double-piston pump, a particularly space-saving and compact design can be obtained.

The cam structures can be configured as grooves or as beads. Hence a particularly effective force transmission from the barrel cam to the pistons of the double-piston pump is able to be obtained. The barrel cam can be drivable by means of a rotary drive. The rotary drive can comprise a planetary gearing arranged, in particular, within the barrel cam. Because the planetary gearing is arranged within the barrel cam, the compactness of the device can be further increased.

The intake opening and the outlet opening can be arranged offset in the longitudinal direction on the cylinder. This constitutes a particularly advantageous design of a double-piston pump. The intake opening can be brought into fluidic connection with the interior of the container. Furthermore, the outlet opening can be brought into fluidic connection with the delivery opening, in particular with the proximal end region of the puncture cannula.

A dosing apparatus of this type can comprise a container, wherein the container is preferably configured as a collapsible bag, syringe or cartridge. These receptacles have the advantage that a liquid is conveyable from these, irrespective of their orientation in relation to gravitational force, without a resulting intake of air through the conveying device. This is in particular advantageous if the dosing apparatus is attached to the body of a patient.

The conveying device can comprise at least one further opening, in particular an intake and/or outlet opening, which is arranged offset in the longitudinal direction on the cylinder. With the conveying device, a large number of further functions can hence be realized. For example, it is possible to connect one or more further containers to the conveying device in order to obtain the reconstitution of a lyophilisate. However, it would also be conceivable for there to be connected to the conveying device an analysis device, for instance, with which, before a preparation is administered to a patient, an analysis is first conducted of a body fluid sucked up through the indwelling cannula. However, the analysis of a fluid to be administered would also be conceivable.

The dosing apparatus can comprise a drive module and a delivery module, which are configured such that they can be connected, and/or disconnected from one another, by a user. The drive module can comprise at least parts of the rotary drive and/or, where appropriate, a fitting drive of the injection device. The delivery module can at least comprise the container and the conveying device and, where appropriate, the injection device. Furthermore, the drive module can also comprise a battery for supplying power to the drives, and a control unit for controlling the device, in particular the drives. Likewise, communication means, via which an external operating unit can be linked to the control unit, can be provided in the drive module.

The drive module and the delivery module can be configured such that the drives can be coupled via appropriate coupling means in simple manner directly or indirectly to the conveying device and/or the injection device. To this end, positive-locking and/or non-positive locking plug-in couplings, for example, can be employed. For simple exchange, the two modules can be able to be connectable to one another, and/or redisconnectable, via a snap coupling, for instance.

This has the advantage that the drive module, which contains no hygienically relevant components, has neither to be sterilized nor installed in a clean room prior to its first use. The manufacturing costs and acquisition costs of the device can hence be reduced. Moreover, the drive module is reusable without difficulty, which also lowers the operating costs of the dosing apparatus. This design also provides more flexibility in respect of design modifications. Although the delivery module, which contains all hygienically relevant components, has to be sterilized, it can be manufactured at lower expense and be disposed of after single usage, since it contains no overly complex components. Since the drive module and the delivery module are configured such that they can be connected and/or disconnected from one another, the use of the delivery device by the user still conceivably remains simple. As a result of this, the costs of acquisition and operation of the dosing apparatus can be lowered, while user friendliness and patient safety remain constant.

In addition, the present invention relates to the use of an above-described dosing apparatus for the, in particular subcutaneous, delivery of a fluid.

Figure 2:
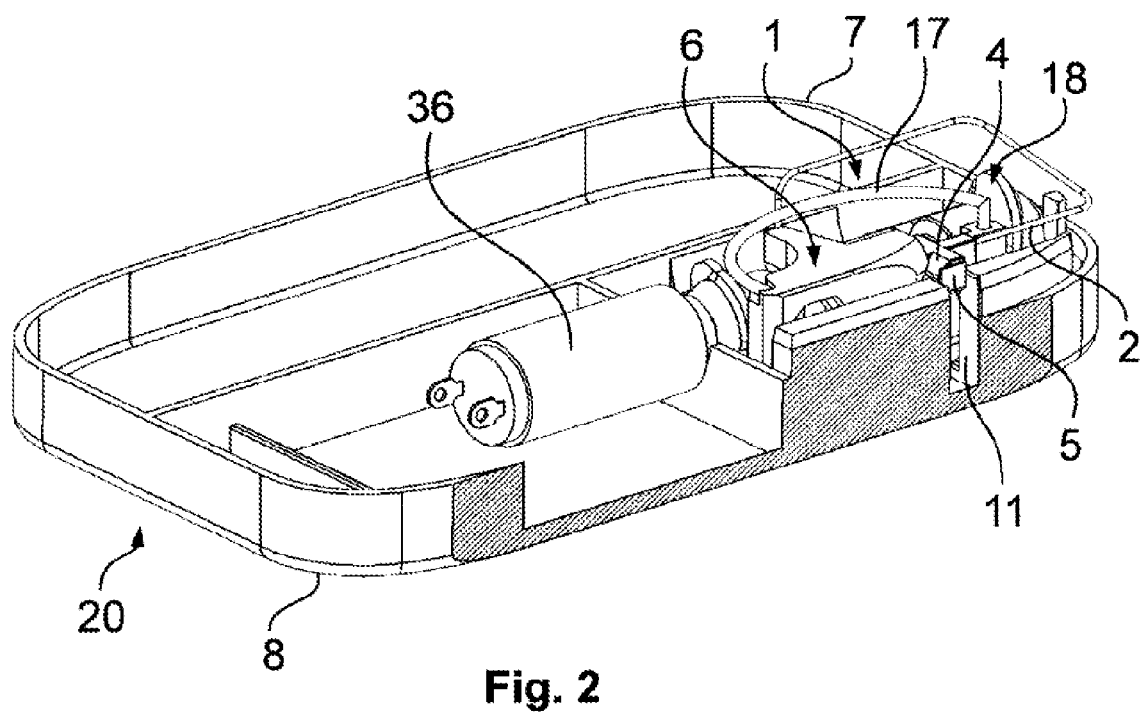
Figure 3:
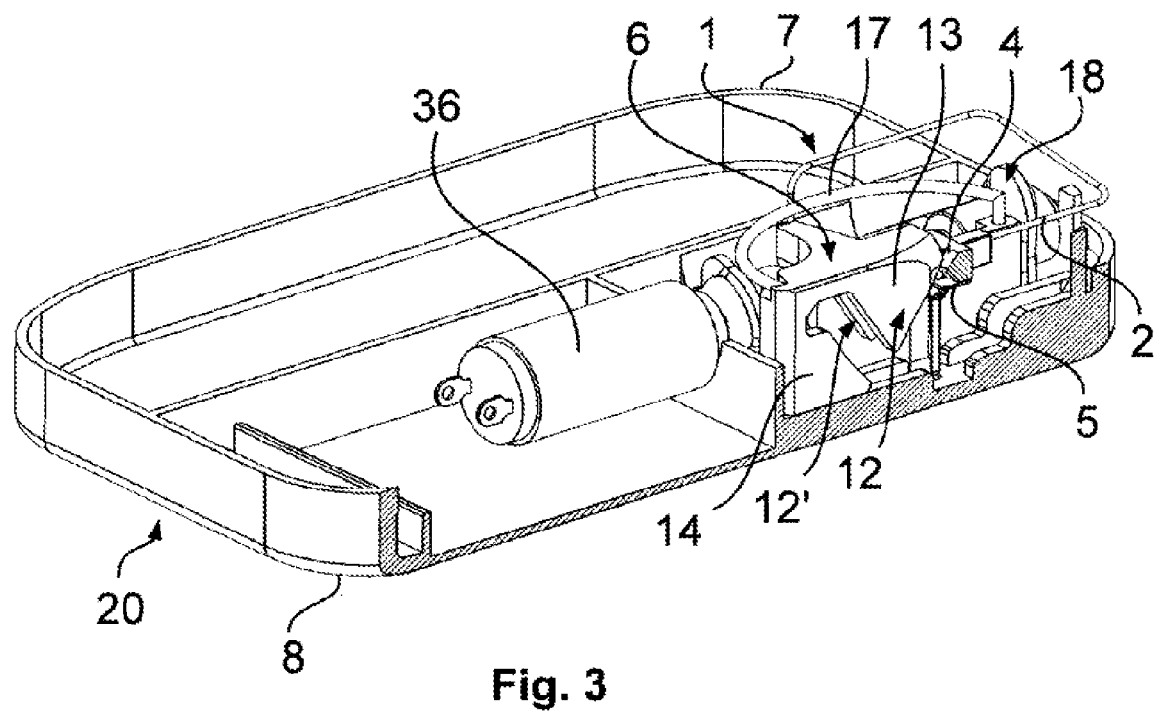
Figure 4:
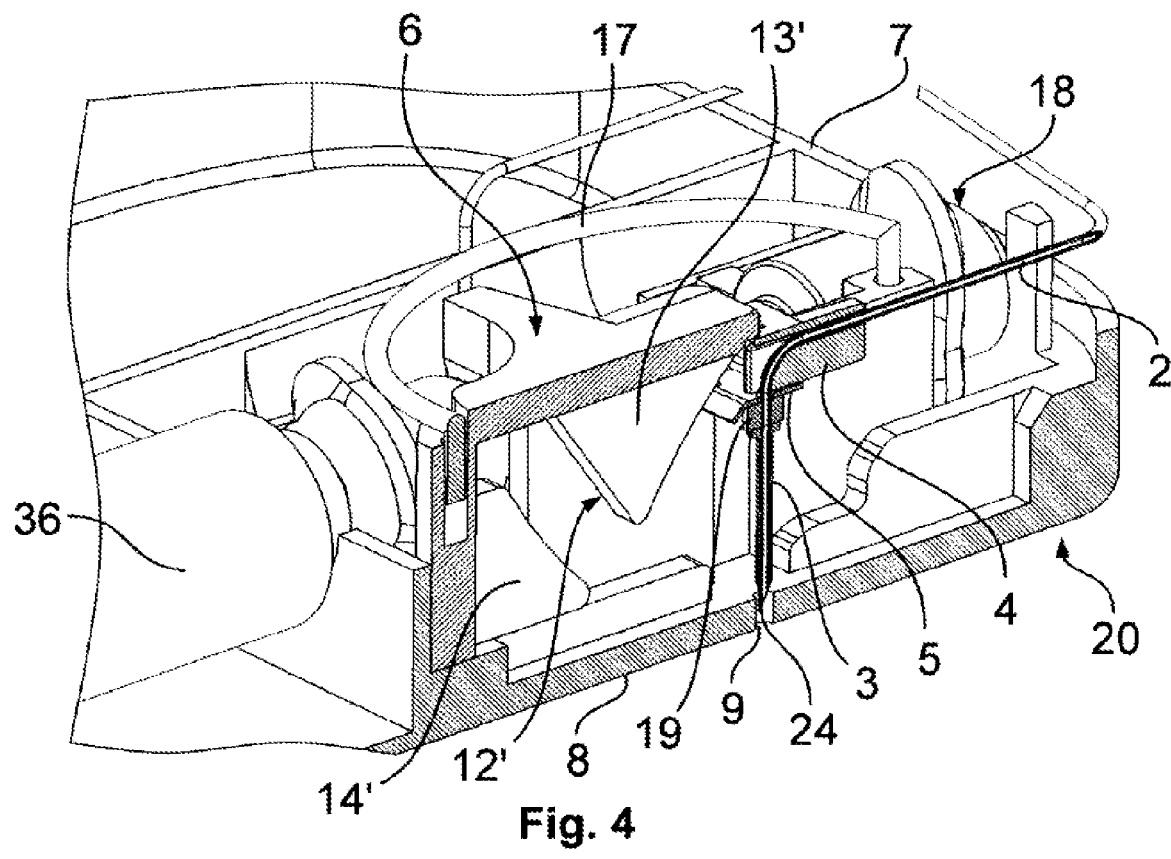
Figure 19:
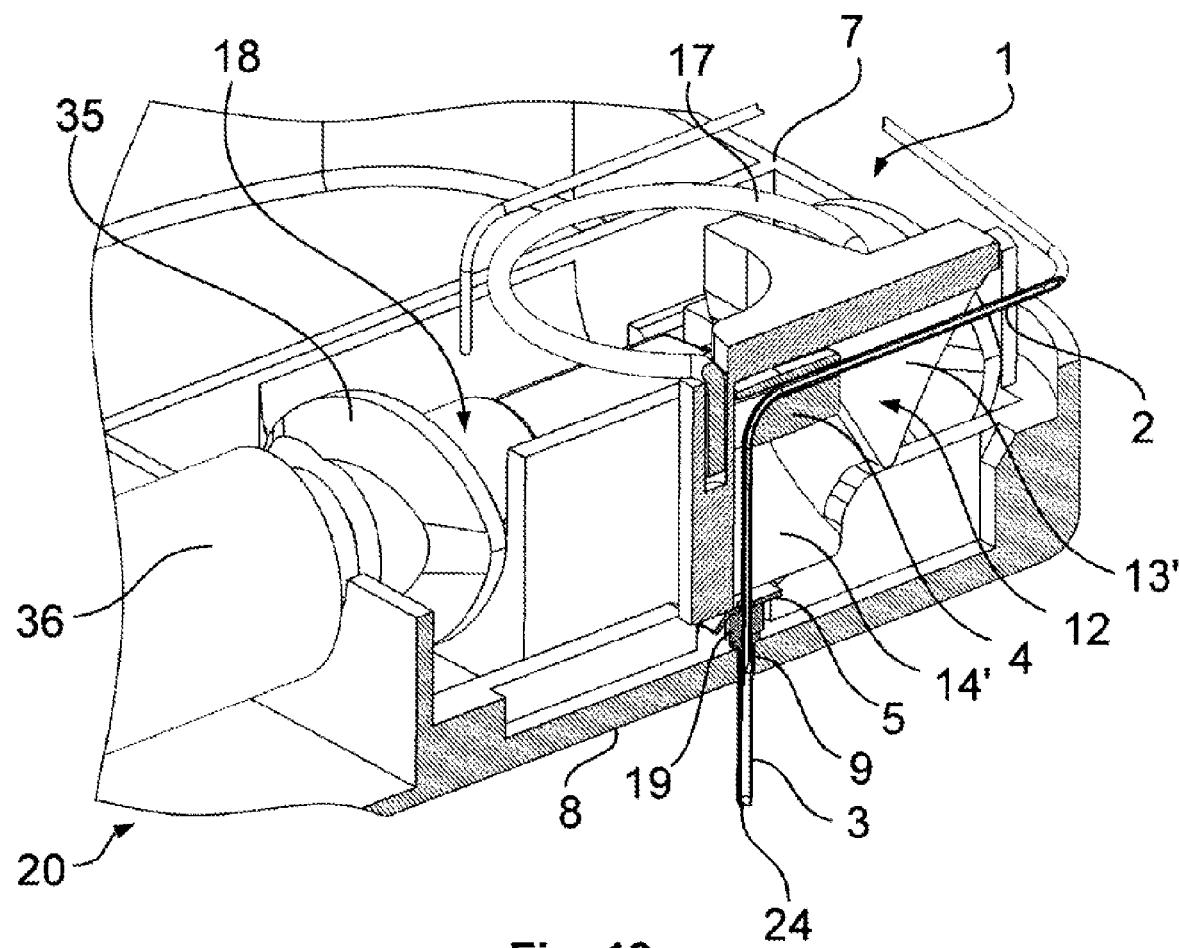
Figure 20:
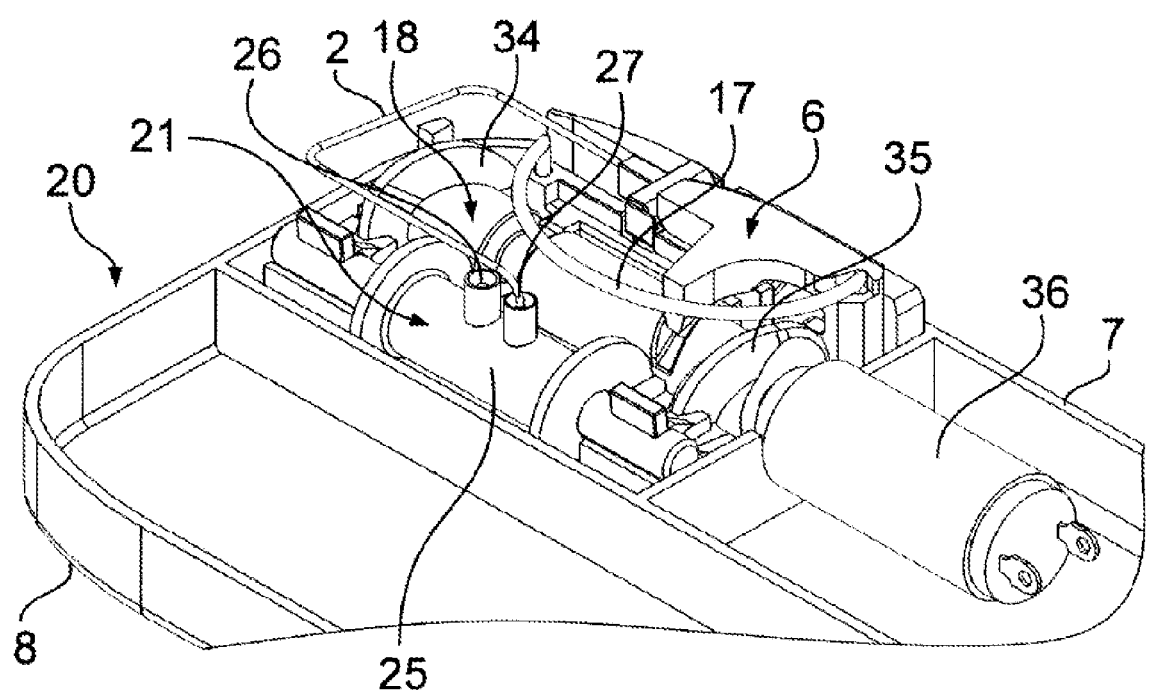
Figure 21:
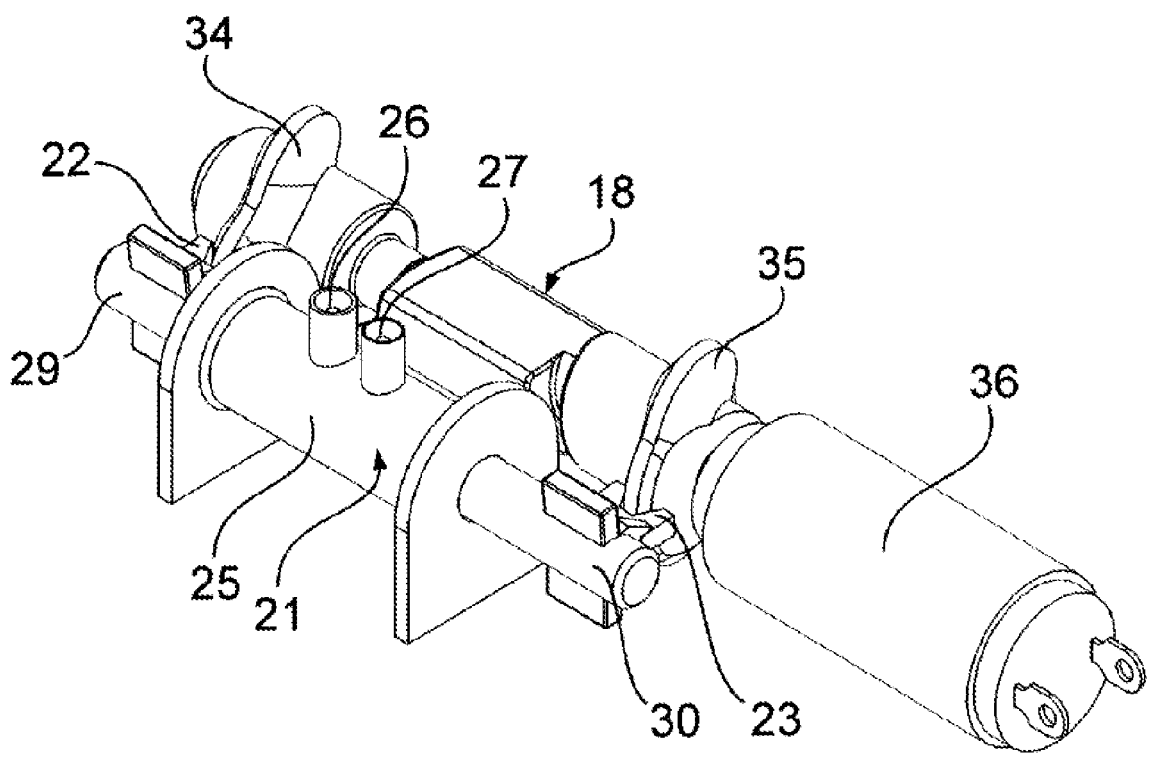
Figure 22:
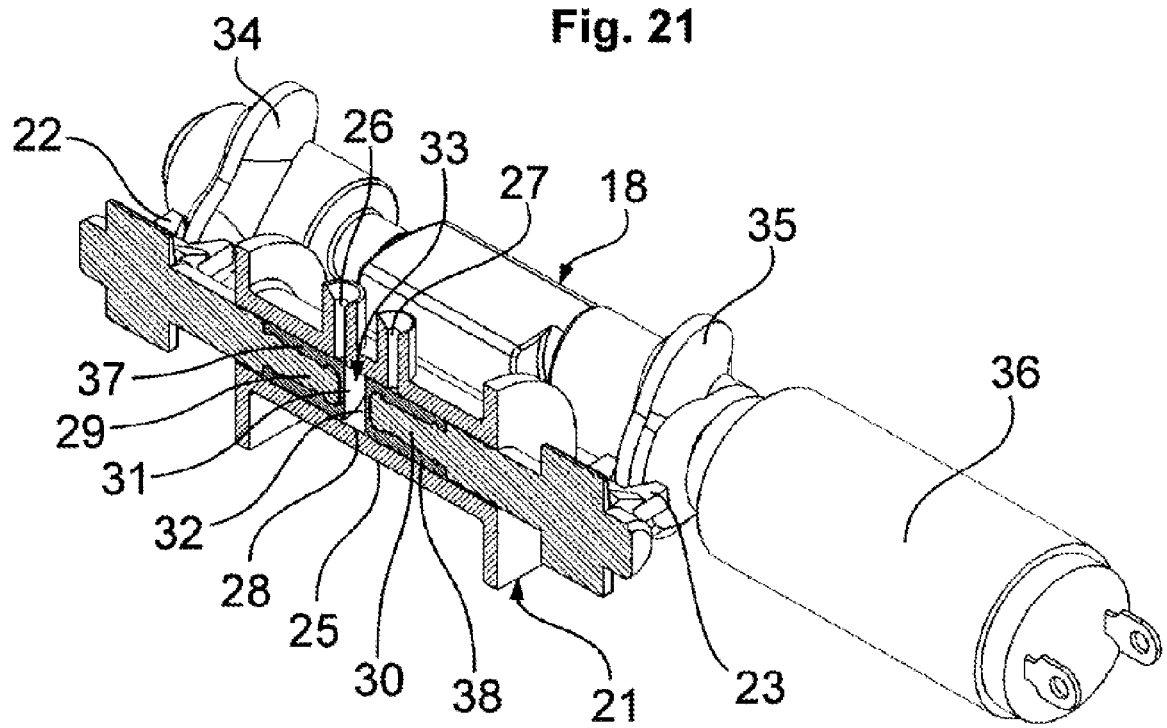
Figure 23:
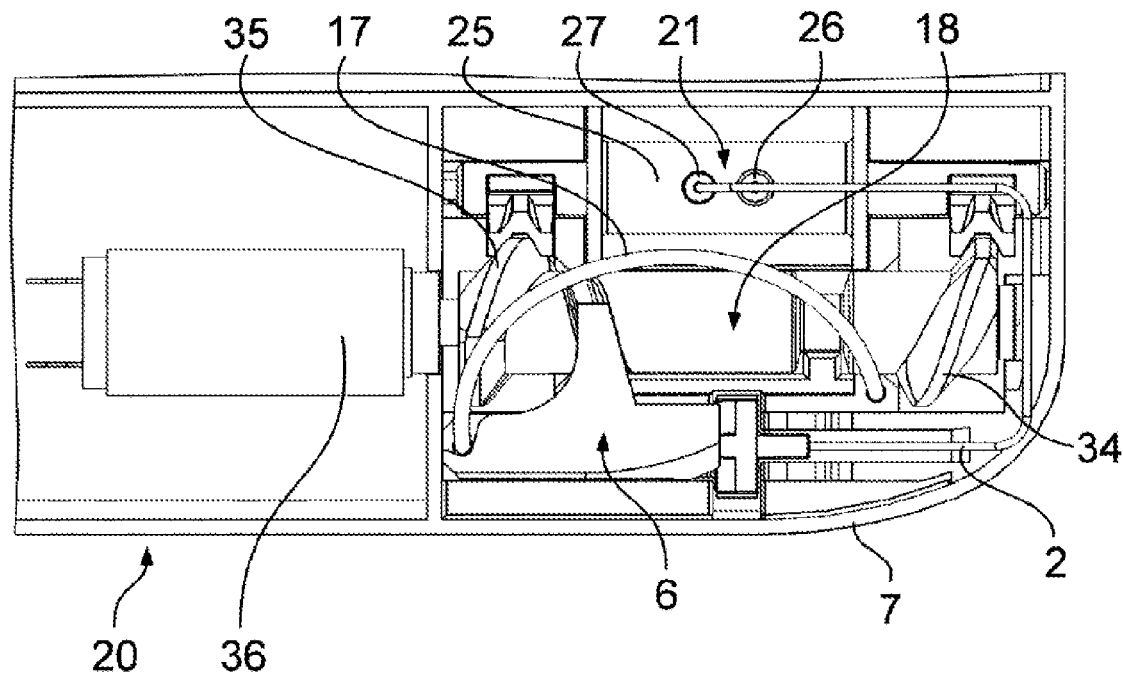
Figure 24:
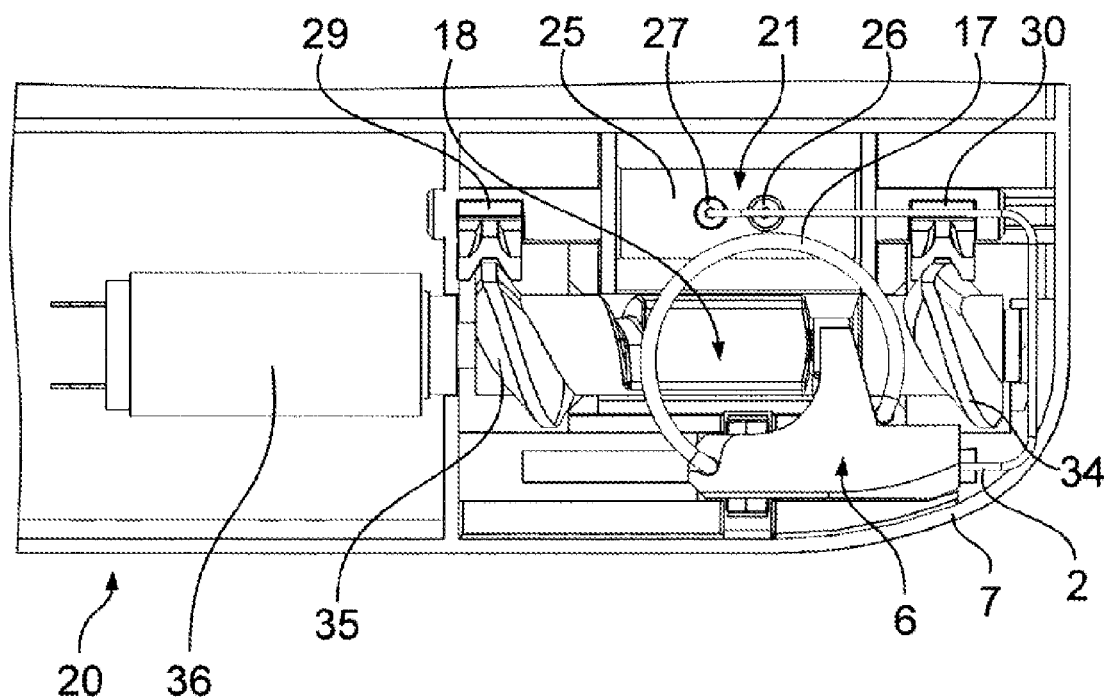

Further advantages and detailed features of the invention emerge from the following description of an illustrative embodiment and from the drawings, wherein, in schematic portrayal:

FIG. 1: shows a perspective representation of a dosing apparatus according to the invention FIG. 2: shows a representation according to FIG. 1, but with a section through the dosing apparatus according to the invention;

FIG. 3: shows a representation according to FIGS. 1 and 2, but with another section through the dosing apparatus according to the invention;

FIG. 4: shows a representation according to FIGS. 1 to 3, but in partial enlargement and with a further section through the dosing apparatus according to the invention;

FIGS. 5-18: show a sequence of steps, which shows the fitting of an indwelling cannula of an injection device according to the invention, wherein the odd-numbered figures respectively show the dosing apparatus in top view, and the following even-numbered figures respectively show the injection device in the corresponding state in spatial representation;

FIG. 19: shows a perspective sectional view of a dosing apparatus according to the invention with an indwelling cannula in dwell position;

FIG. 20: shows a perspective representation of a dosing apparatus according to the invention with injection device and conveying device;

FIG. 21: shows a perspective representation of the conveying device of a dosing apparatus according to the invention;

FIG. 22: shows a section through a representation according to FIG. 21;

FIG. 23: shows a top view of a segment of a dosing apparatus according to the invention in a first operating position;

FIG. 24: shows a representation according to FIG. 23, but with the dosing apparatus in a second operating position;

FIGS. 25-28: show a perspective representation of a sequence of steps, which shows the fitting of an indwelling cannula of an alternative illustrative embodiment of an injection device according to the invention.

In FIG. 1, a dosing apparatus 20 according to the invention is represented, wherein, for better clarity, only the injection device 1 with the barrel cam 18 and the rotary drive 36 are represented. The conveying device 21 and further components of the dosing apparatus 20, such as, for instance, a control unit or a battery, are omitted for better clarity. The dosing apparatus 20 has a housing 7, the bottom side of which forms a contact surface 8 for attaching the apparatus 20 to a patient. The injection device 1 comprises the control element 6, which can be brought into operative connection with the first runner 4 and the second runner 5.

The control element 6 is pretensioned via the spring element 17. However, it is held back by the barrel cam 18 held back against the pretension.

In the sectional view according to FIG. 2 can clearly be seen the linear guide 11 with which the first runner 4 and the second runner 5 are guided. In FIG. 3, the control element 6 can be seen. It is apparent that this is configured as a pair of congruent, displaceable cam carriers 12, 12'. Of the front cam carrier 12, both portions 13 and 14 are visible.

In FIG. 4, that segment of the dosing apparatus comprising the injection device 1 is shown in enlarged representation. In comparison to FIGS. 2 and 3, the sectional plane is offset further to the rear, so that this now runs in the longitudinal direction through the puncture cannula 2 and the indwelling cannula 3. Since the section also runs through the control element 6, the rear cam carrier 12', comprising the two portions 13' and 14', is now visible. It can be seen that the puncture cannula 2, in the starting position of the injection device 1, runs in the longitudinal direction within the indwelling cannula 3. On the bottom side of the housing 7 is provided a fitting opening 9, which penetrates the contact surface 8. The second runner 5 is designed as a holding plate, to which is attached a seal 19 which seals the transition between the fitting cannula 2 and the indwelling cannula 3.

Figure 5:
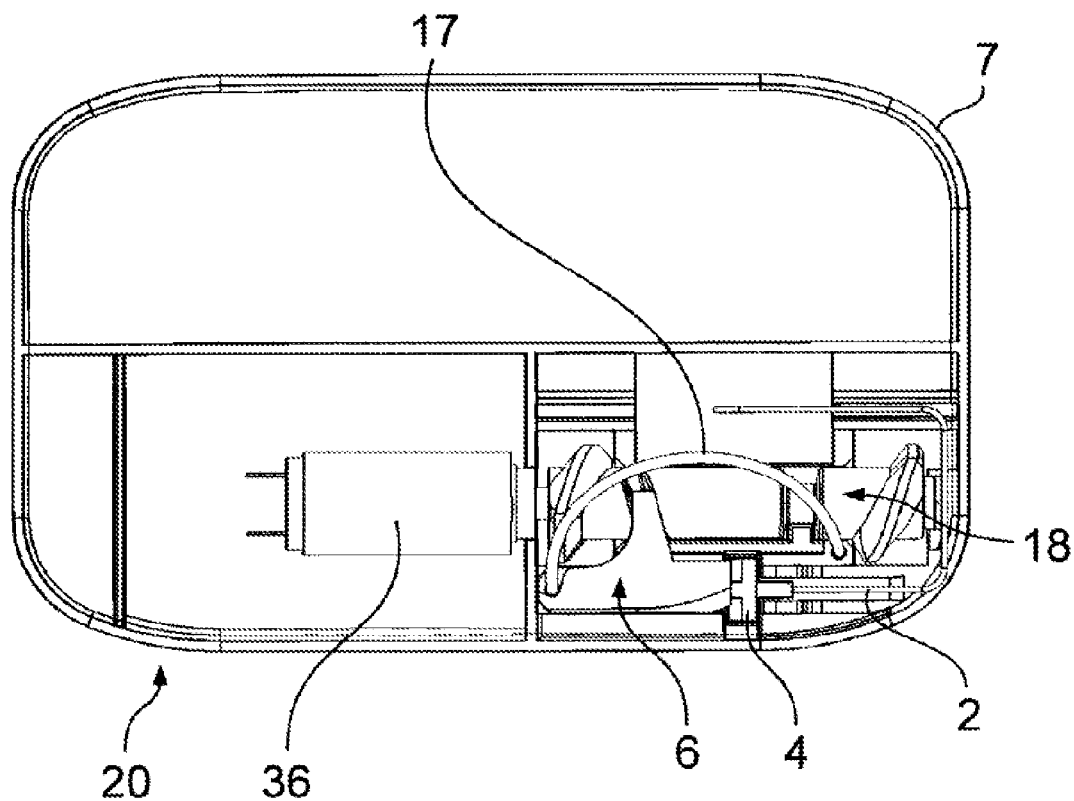
Figure 6:
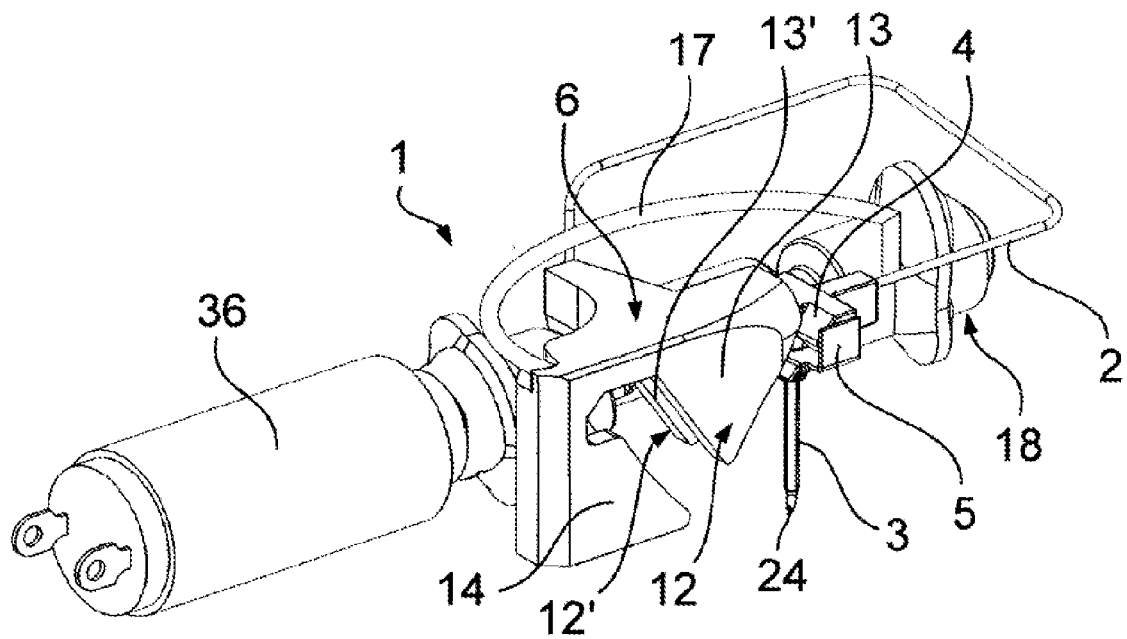

FIGS. 5 and 6 show the injection device 1 in its starting position. The barrel cam 18 has still not performed a rotary movement. In FIG. 6, it can be seen that the first portion 13 of the cam carrier 12 and the first portion 13' of the second cam carrier 12' are not yet in operative connection with the first runner 4 and the second runner 5.

Figure 7:
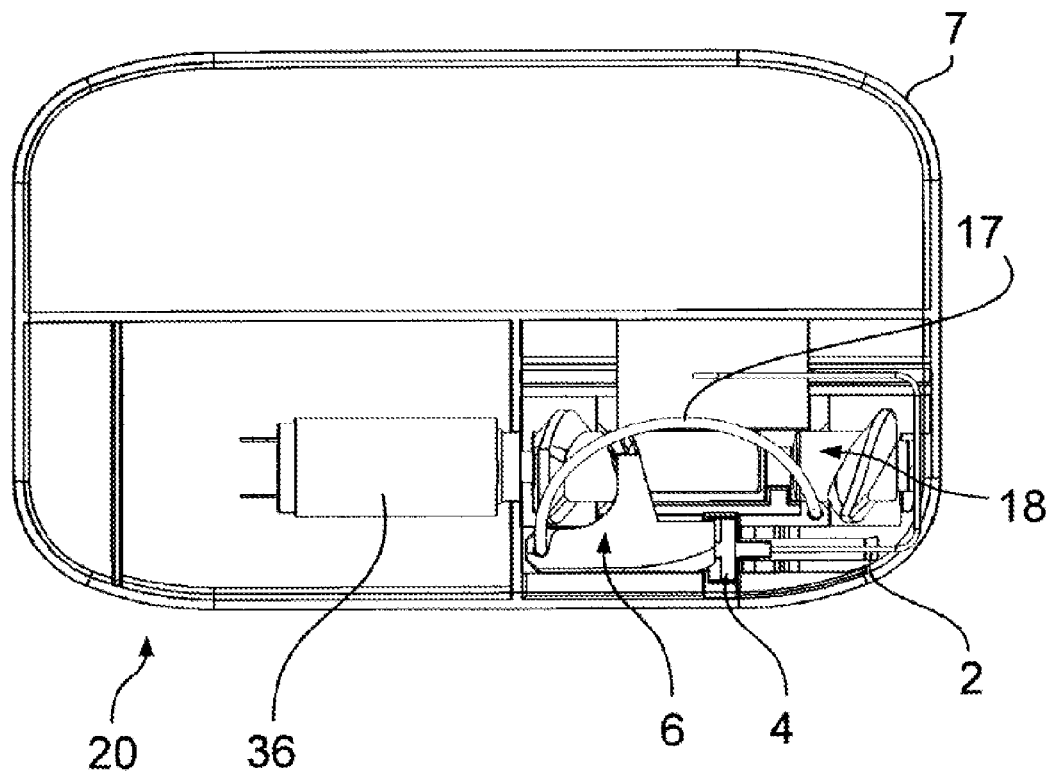
Figure 8:
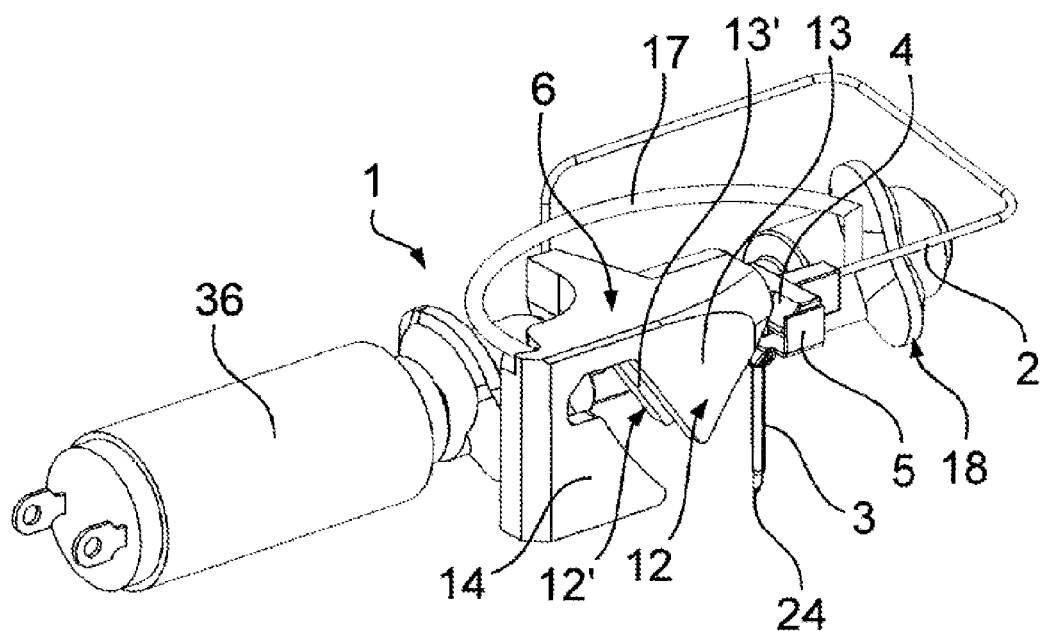

FIGS. 7 and 8 show the injection device 1 at the beginning of the fitting process. The barrel cam 18 has already rotated through a few degrees. The first regions 13, 13' of the cam carriers 12, 12' are now in operative connection with the second runner 5.

Figure 9:
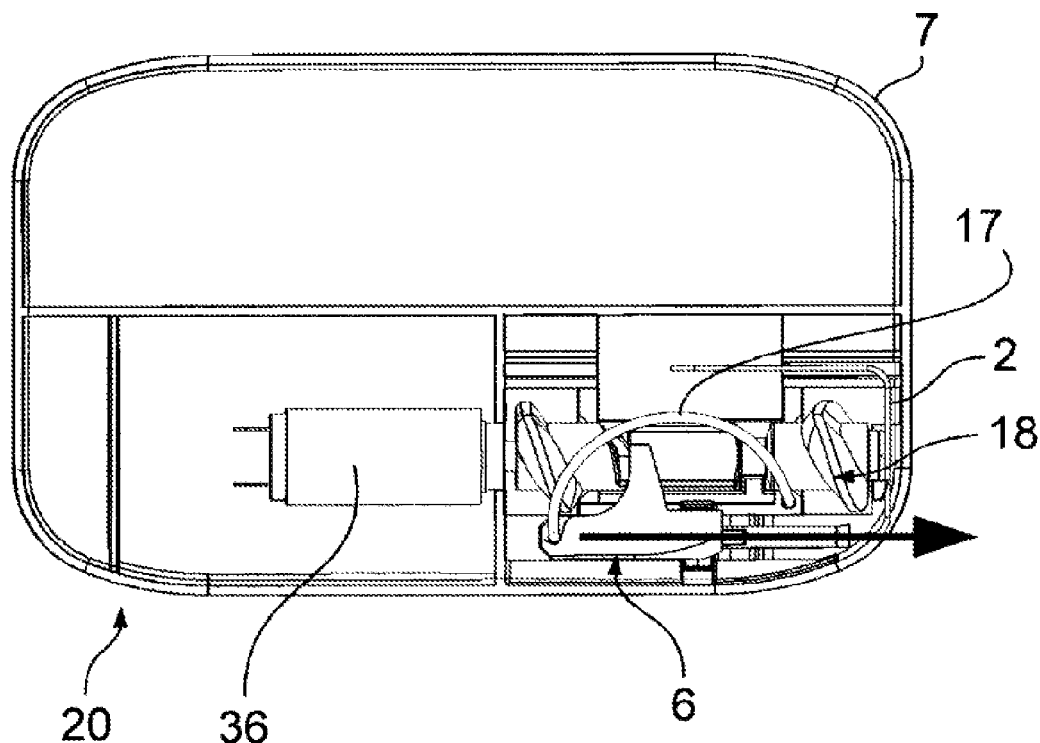
Figure 10:
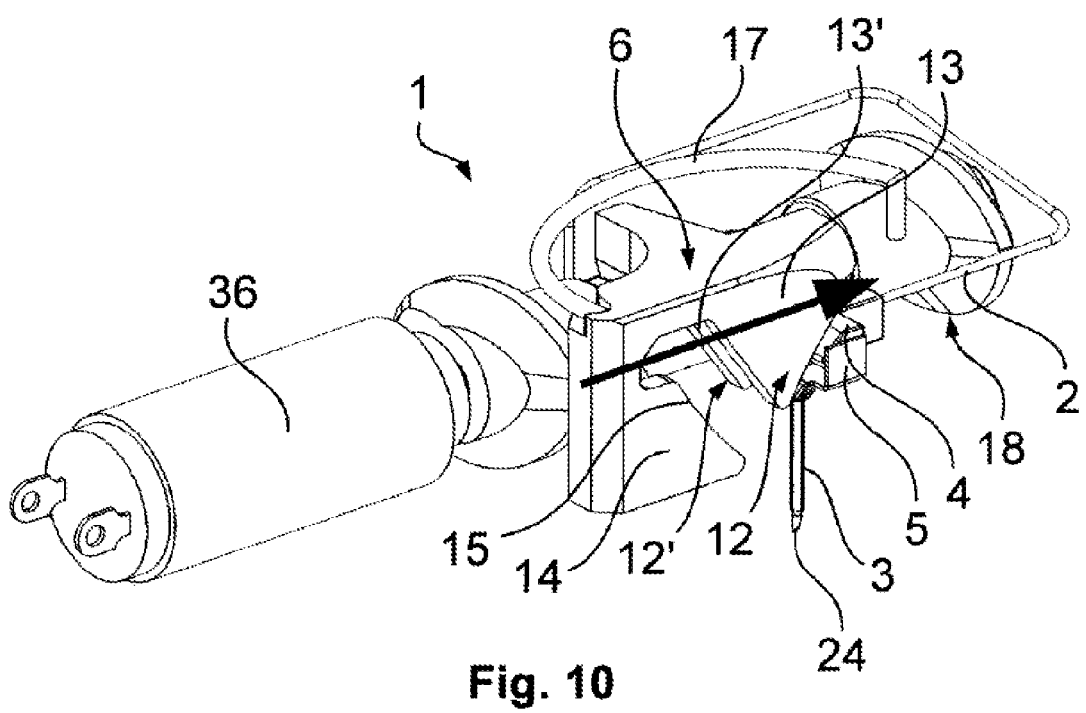

FIGS. 9 and 10 show the injection device 1 during the actual fitting process. In FIG. 9, it can be seen that the barrel cam 18 has now rotated to the point where it no longer holds back the control element 6 against the pretension of the spring element 17. Accordingly, the control element 6 can move freely, whereby the first portions 13, 13' of the cam carriers 12, 12' press the first runner 4 and the second runner 5 downward.

Figure 11:
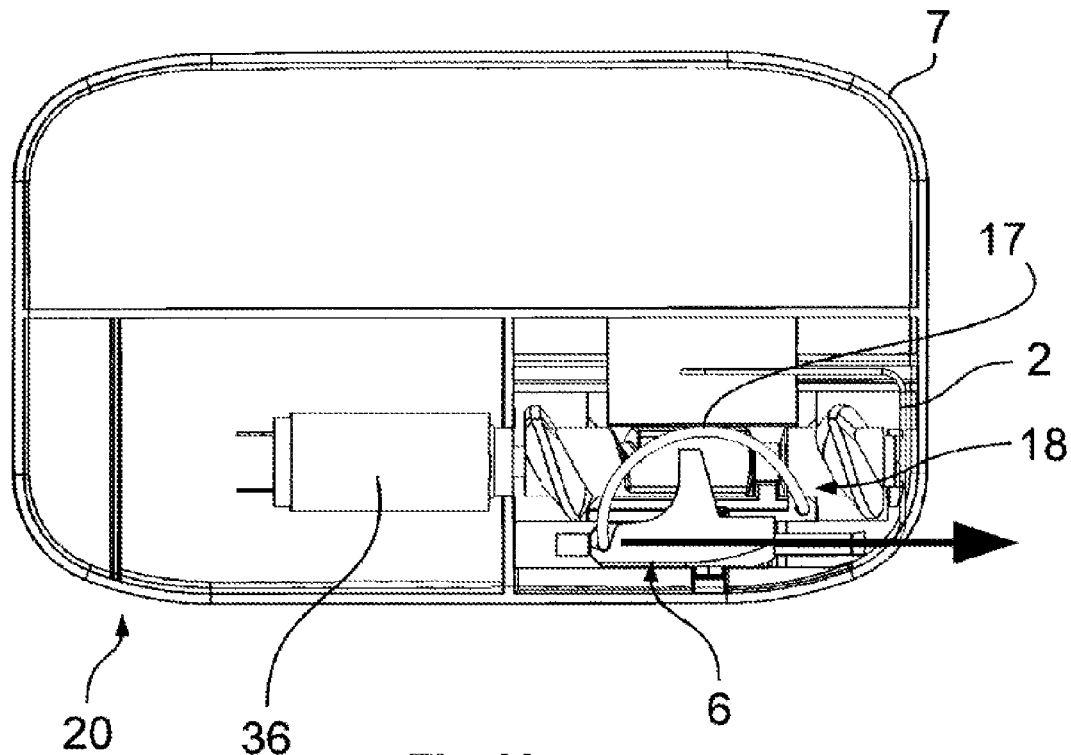
Figure 12:
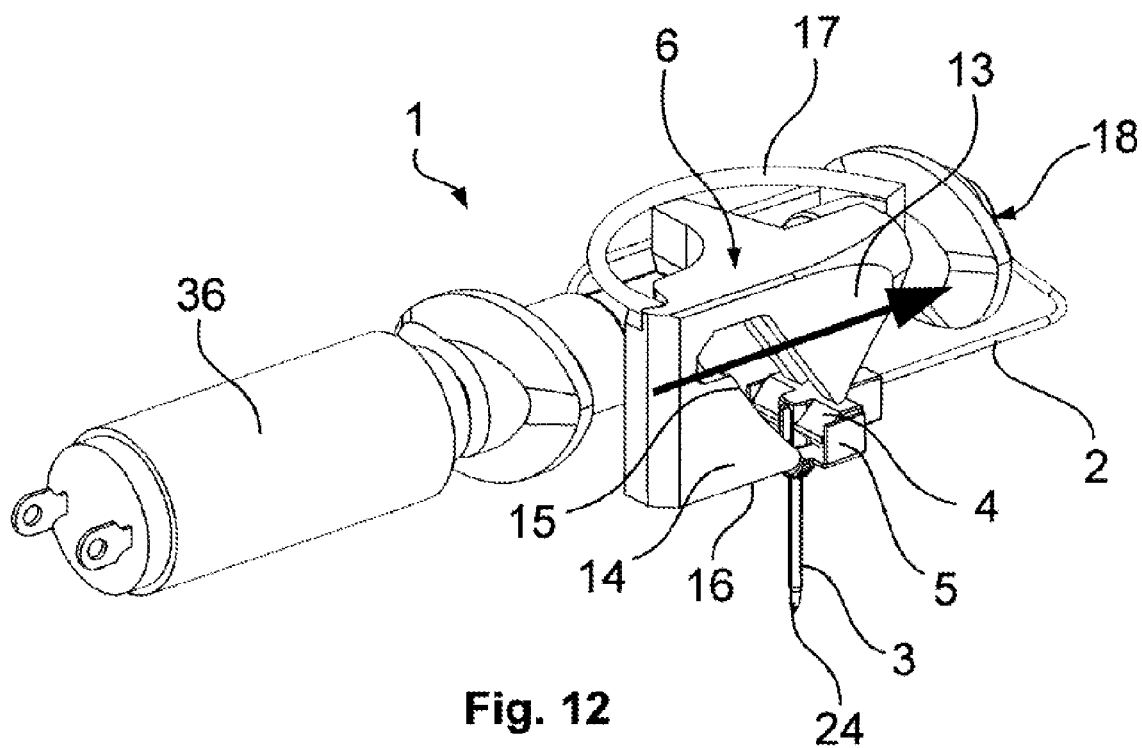

In FIGS. 11 and 12, the first runner 4 and the second runner 5 have arrived at their lower stop point. The puncture cannula 2 is hence fitted in place. In FIG. 11 it can be seen that the control element 6 has only covered about half of its path and moves onward under the spring preload.

Figure 13:
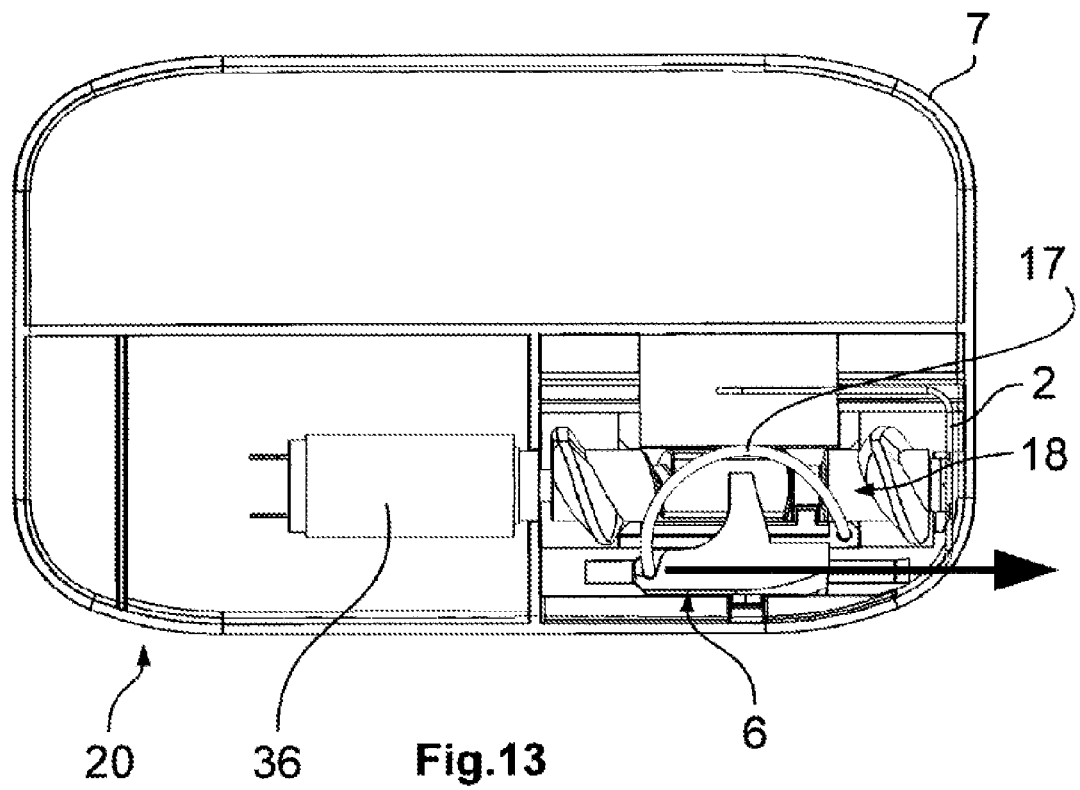
Figure 14:
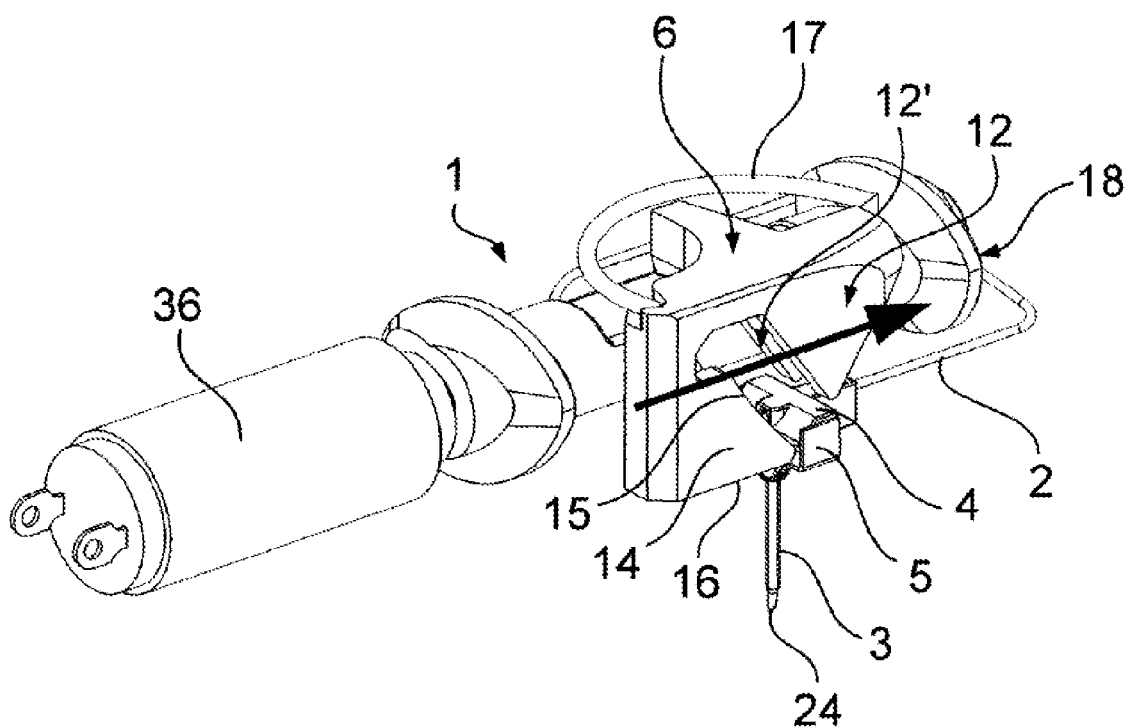

In FIGS. 13 and 14, the first runner 4 and the second runner 5 are now in operative connection with the second portions 14, 14' of the cam carriers 12, 12'. The top side 15 and 15', respectively, of the second portions 14, 14' here acts on the first runner 4, whereby the fitting cannula 2 is withdrawn upward from the indwelling cannula 3. On the second runner 5 acts the bottom side 16 and 16', respectively, of the second portions 14, 14'. This leads to a locking of the second runner 5, and hence of the indwelling cannula 3, in its dwell position.

Figure 15:
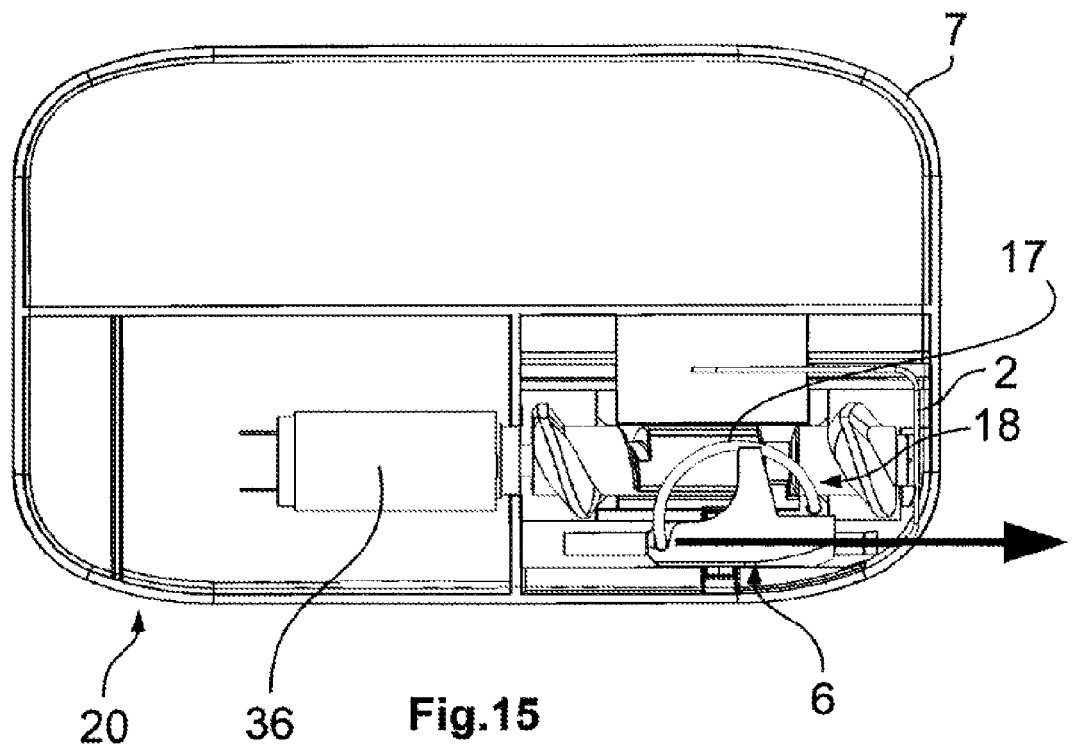
Figure 16:
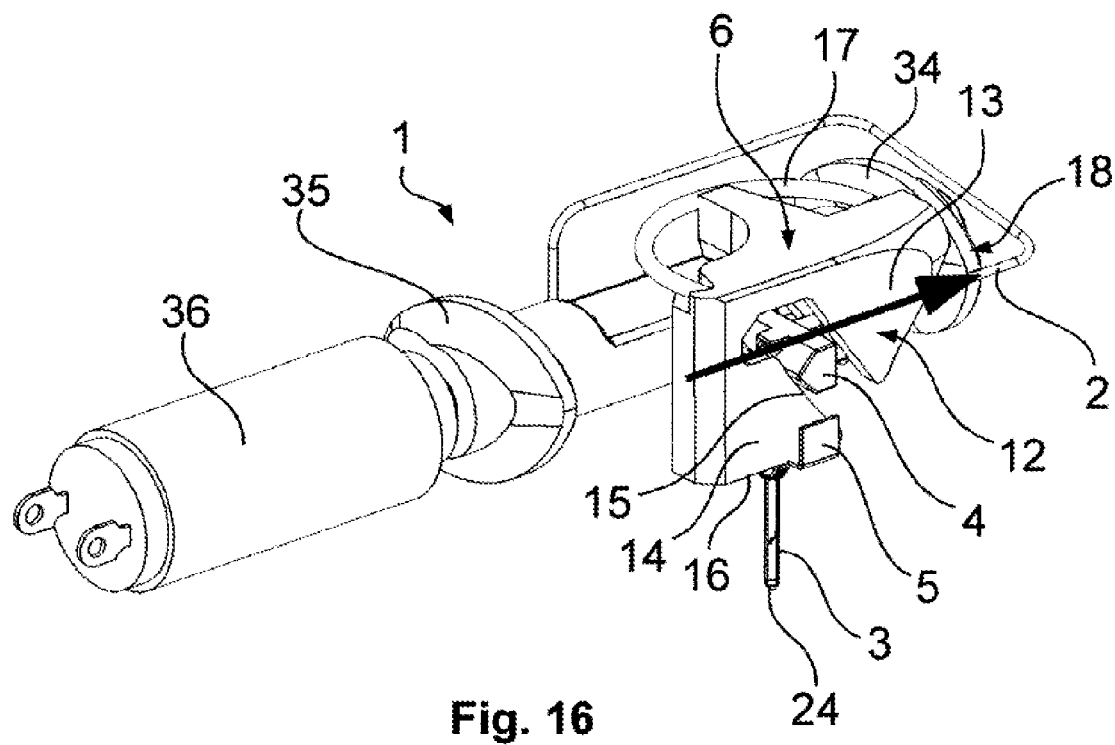

FIGS. 15 and 16 show the upward withdrawal of the fitting cannula 2 from the indwelling cannula 3. Here too, the first runner 4 is pressed upward from the bottom side 15 and 15', respectively, of the second portions 14, 14'.

Figure 17:
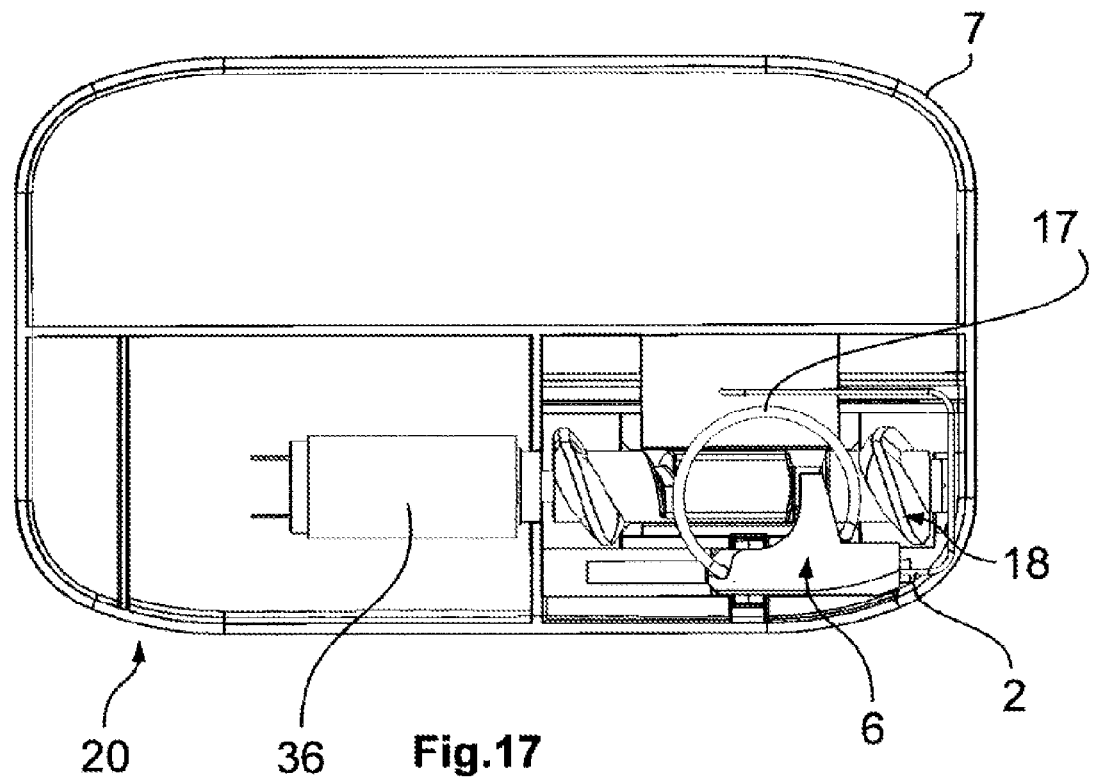
Figure 18:
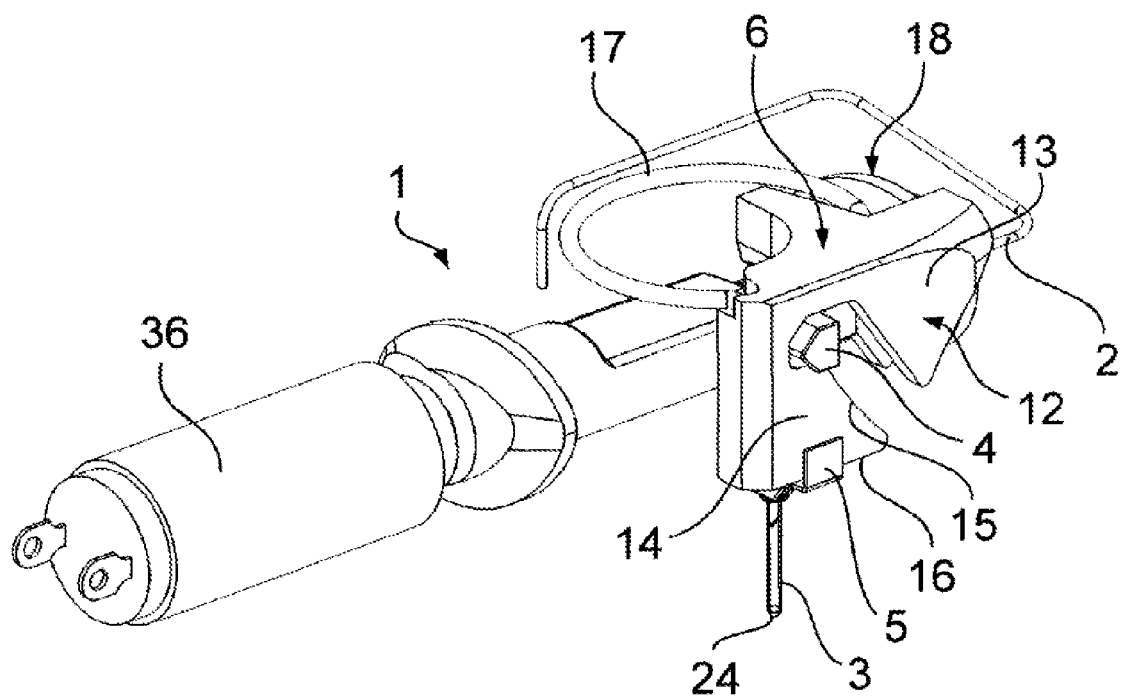

In FIGS. 17 and 18, the control element 16 has reached its stop on the barrel cam 18. It is no longer further movable by the spring element 17. It can be seen that the first runner 4 has reached its end position, whereas the second runner 5, and hence the indwelling cannula 3, are still locked in the dwell position.

FIG. 19 shows a sectional view of the injection device 1 in the dosing apparatus 20 in its end position. The indwelling cannula 3 now juts out of the fitting opening 9, while the puncture cannula 2 is substantially withdrawn. Also discernible is the sealing element 19, which is squeezed by the second runner 5 and the housing 7 of the apparatus 20. As a result, a better seal at the transition from the fitting cannula 2 to the indwelling cannula 3 can be obtained.

FIG. 20 shows a spatial representation of the dosing apparatus 20 according to the invention, though now also with the conveying device 21. It can be seen that the barrel cam 18 is in operative connection both with the injection device 1 and with the conveying device 21. The barrel cam 18 hence serves simultaneously to control the injection device 1 and to drive the conveying device 21. The proximal end region of the puncture cannula 21 is fluidically connected to the exit opening 27 of the conveying device 21.

In FIG. 21, the conveying device 21, in combination with the barrel cam 18 and the rotary drive 36, is represented in isolation. It can be seen that the conveying device 21 is designed as a double-piston pump comprising the cylinders 25 and the pistons 29 and 30. Respectively attached to the pistons 29 and 30 are fork-shaped elements 22 and 23, in which bead-like cam elements 34 and 35 of the barrel cam 18 engage.

FIG. 22 shows a diagram corresponding to FIG. 21, with a section along the longitudinal center axis of the cylinder 25. It can be seen that the pistons 29 and 30 are equipped in their end regions with the sealing elements 37 and 38. The end faces 31 and 32 of the pistons 29 and 30 form jointly with the inner wall 28 of the cylinder 25 a variable fluid volume 33. The entry opening 26 and the outlet opening 27 of the conveying device 21 are provided offset in the longitudinal direction on the cylinder 25.

FIGS. 23 and 24 show a top view of a segment of the dosing apparatus according to the invention before and after the fitting process. It can be seen that the fitting process is triggered with the rotary drive 36 via a rotation of the barrel cam 18. The displacement of the control element 6 is realized, however, mainly by the preload of the spring element 17. Through the rotation of the barrel cam 18, a longitudinal displacement of the cylinders 29 and 30 within the piston 25, moreover, ensues.

Figure 25:
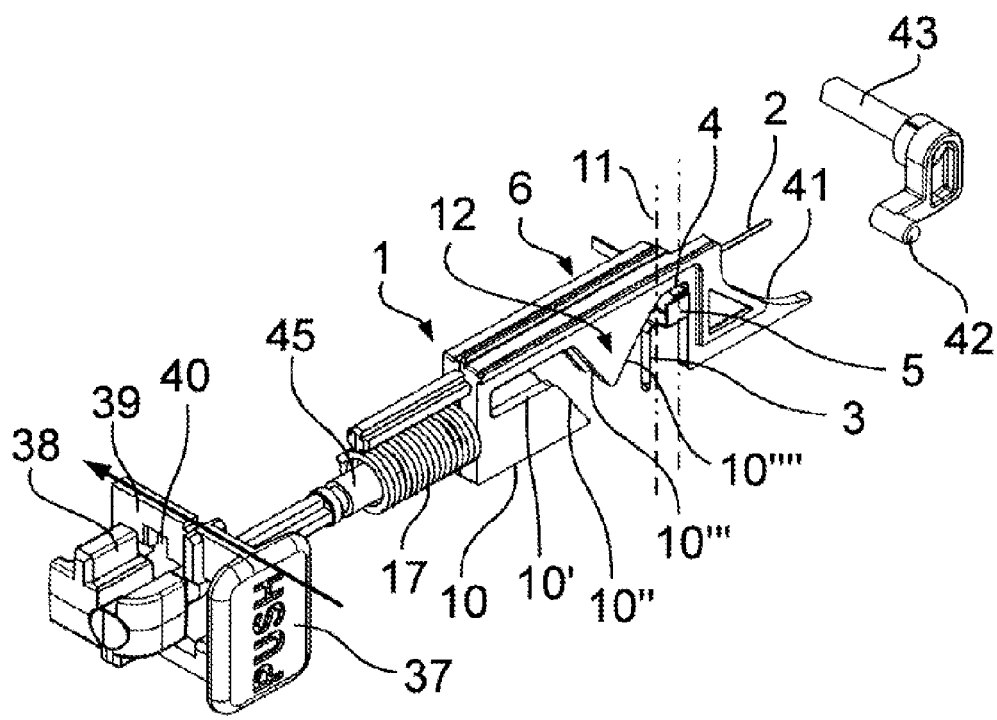

FIGS. 25 to 28 show an alternative illustrative embodiment of an injection device 1 according to the invention. In FIG. 25, said device 1 can be seen in its starting position. The control element 6 is pretensioned via a spring element 17, which is here configured as a helical spring. The control element 6 is held back against the pretension by a stop element 38, which rests on a stop plate 39. By actuation of the release button 37 (in the arrow direction), the stop plate 39 is displaced in a direction perpendicular to the direction of displacement of the control element 6. As a result, the stop element 38 can slide through the recess 40 in the stop plate 39 and trigger the actual fitting process.

In FIG. 25 are additionally illustrated the cam surfaces 10, 10', 10", 10''', 10'''' of the cam carrier 12, which prescribe the movement of the first runner 4 and of the second runner 5 over the control area.

In FIGS. 25 to 28, only parts of the injection device 1 are represented. The non-shown parts generally correspond to those according to FIGS. 1 to 25. In particular, the linear guides 11 (indicated in FIG. 25 only in dashed representation) are substantially identical to those in the preceding figures.

Figure 26:
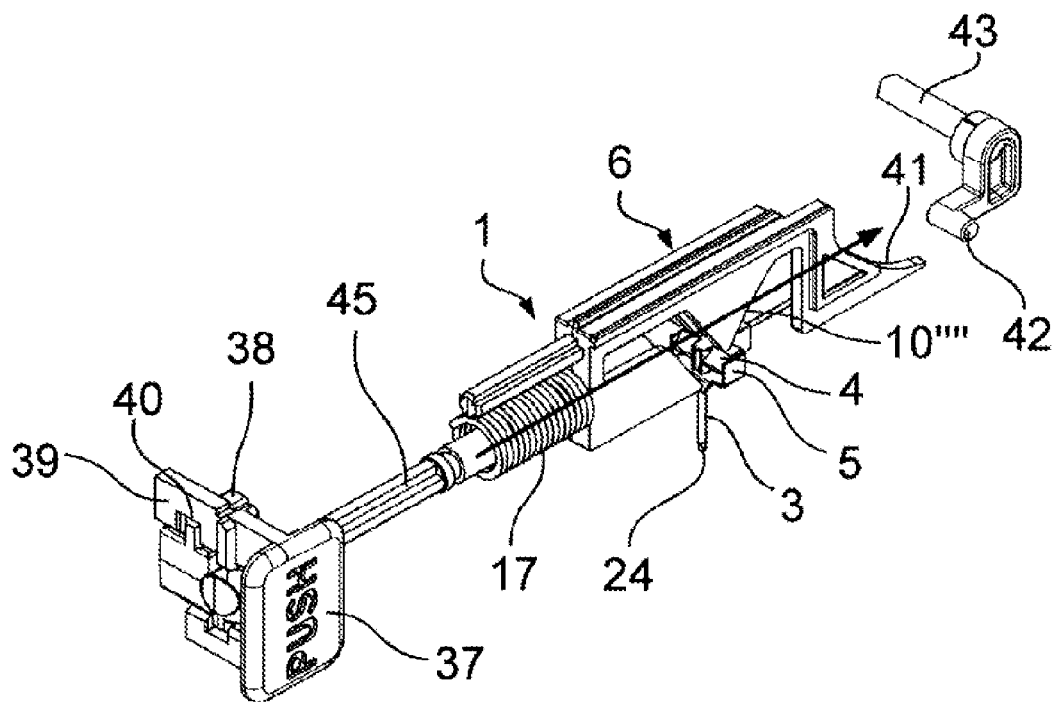

In FIG. 26, the control element 6 is already displaced over the first part of the control area (in the arrow direction). This has led, by means of the surface 10'''', to a simultaneous-equidirectional displacement of the two runners 4, 5, and hence to a fitting of the indwelling cannula 3 with the aid of the puncture cannula 2.

Obviously, during the displacement of the control element 6, an expansion of the helical spring 17 ensues. For technical drawing reasons, this latter is shown in FIGS. 25 to 28, however, always in the compressed state.

Figure 27:
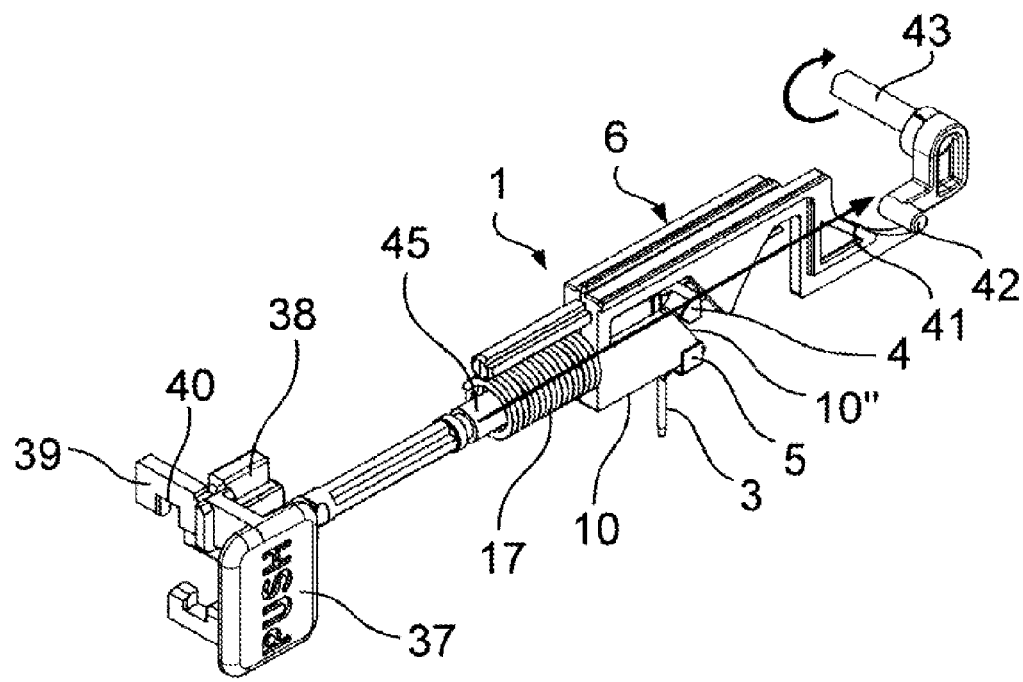
Figure 28:
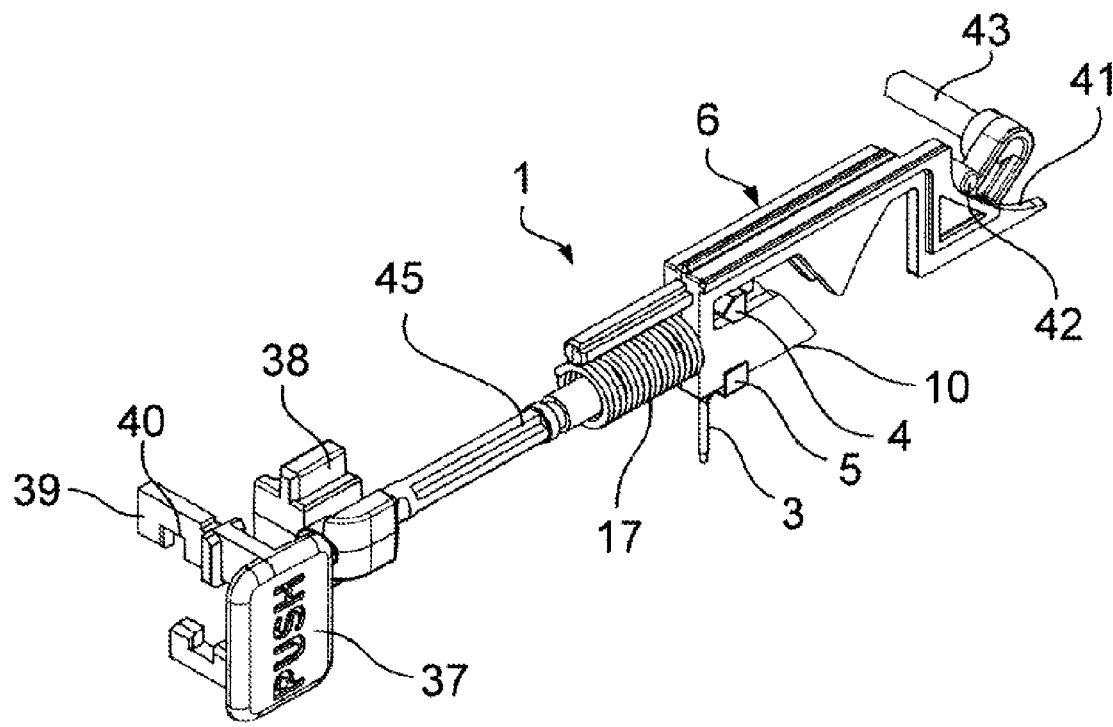

FIG. 27 shows the displacement of the control element 6 over a second part of the control area. On the one hand, a blocking of the second runner 5, designed as a holding plate, and hence a holding of the indwelling cannula 3 in the dwell position, is here obtained merely by action, especially downpressing, by the control element 6 with the cam surface 10. On the other hand, by means of the cam surface 10", a withdrawal of the puncture cannula 2 from the distal end region of the indwelling cannula 3 is obtained.

The control element 6 has an additional cam surface 41, which in the second part of the control area acts on the lever element 42. The lever element 42 is thereby movable from the first position, shown in FIG. 27, into a second position, depicted in FIG. 28, whereby a rotation of a pivot pin 43 ensues. The control element 6 can hence control further functions of an appropriate device, for instance a dosing apparatus. Thus, an activation of a valve device or conveying device in order to conduct a fluid to the injection device can be realized.

The invention claimed is:

1. A dosing apparatus for subcutaneous, intradermal, intramuscular or intraperitoneal delivery of a fluid, the dosing apparatus comprising:

a conveying device for conveying the fluid out of an interior of a container, and the fluid being conveyable by means of the conveying device from the container to a delivery opening;

an injection device for subcutaneous delivery of the fluid, comprising a puncture cannula, and an indwelling cannula;

the conveying device being designed as a positive displacement pump, the conveying device comprising a cylinder, having at least one intake opening and at least one outlet opening on a cylinder inner wall, and a first piston and a second piston, the first piston and the second piston are mounted displaceably within the cylinder in a longitudinal direction, and the first and second pistons delimit between their respective end faces, jointly with a portion of the cylinder inner wall, a variable fluid volume; and a barrel cam having a first cam structure and a second cam structure arranged alongside the cylinder, wherein the first cam structure is in operative connection with the first piston via a first fork-shaped element and the second cam structure is in operative connection with the second piston via a second fork-shaped element, and wherein, upon rotation of the barrel cam, the first cam structure rotates within the first fork-shaped element to thereby prescribe a stroke movement of the first piston and the second cam structure rotates within the second fork-shaped element to thereby prescribe a stroke movement of the second piston, wherein the barrel cam is in operative connection both with the injection device and with the conveying device such that the barrel cam serves simultaneously to control the injection device and to drive the conveying device, and wherein a proximal end region of the puncture cannula is fluidically connected to the at least one outlet opening of the conveying device.

2. The dosing apparatus according to claim 1, wherein in a starting position a distal end region of the puncture cannula runs coaxially inside the indwelling cannula, the injection device comprises displaceably mounted first and second runners, the first runner is connected to the puncture cannula and the second runner to the indwelling cannula, the injection device further comprises a control element, which is movable over a predefined control area and which, for displacement of the first runner and of the second runner, is brought into operative connection with the first and second runners, and the control element is configured such that, in a first part of the control area, the control element effects equidirectional displacement of the first and second runners, and, in a second part of the control area, effects blocking of the second runner, and hence holding of the indwelling cannula in a dwell position, and a back shift of the first runner, and hence withdrawal of the puncture cannula from a distal end region of the indwelling cannula into an end position, and the first and second runners are mounted displaceably via a guide device.

3. The dosing apparatus according to claim 2, wherein the puncture cannula and the indwelling cannula, in the starting position, are arranged substantially within a housing and, for the fitting of the indwelling cannula, are extensible from the housing through a fitting opening in a contact surface.

4. The dosing apparatus according to claim 2, comprising a drive module and a delivery module, which are configured such that the drive module and the delivery module are at least one of connectable to or disconnectable from one another, by a user, the drive module comprises at least parts of a rotary drive, and, where appropriate, a fitting drive of the injection device, and the delivery module comprises at least the container and the conveying device.

5. The dosing apparatus according to claim 2, wherein the first and second runners are mounted displaceably, via the guide device.

6. The dosing apparatus according to claim 5, wherein the control element is movably mounted in a direction substantially perpendicular to that of the linear guide device.

7. The dosing apparatus according to claim 2, wherein the first and second runners are mounted displaceably, via the guide device, and the guide device is oriented in a fitting direction parallel to the distal end regions of the puncture cannula and of the indwelling cannula.

8. The dosing apparatus according to claim 7, wherein the control element is movably mounted in a direction substantially perpendicular to that of the guide device.

9. The dosing apparatus according to claim 2, wherein the control element is configured as a displaceable cam carrier.

10. The dosing apparatus according to claim 2, wherein the control element comprises first and second portions, the first portion effects an equidirectional displacement of the first and second runners, and the second portion effects blocking of the second runner, and hence holding of the indwelling cannula in the dwell position, as well as the backshift of the first runner, and hence withdrawal of the puncture cannula from the distal end region of the indwelling cannula into the end position, and sides of the second portion act on the first and second runners.

11. The dosing apparatus according to claim 1, wherein the at least one intake opening is brought into fluidic connection with the interior of the container.

12. The dosing apparatus according to claim 11, comprising a plurality of containers in addition to said container, and each intake opening is brought into fluidic connection with the interior of a separate container of said plurality of containers which is assigned to said intake opening.

13. The dosing apparatus according to claim 1, wherein the at least one outlet opening is brought into fluidic connection with the delivery opening.

* * * * *